United States Patent [19]

Knodle et al.

[11] Patent Number: 5,369,277
[45] Date of Patent: Nov. 29, 1994

[54] INFRARED SOURCE

[75] Inventors: Daniel W. Knodle, Seattle; Paul K. Graham, Renton; Lawrence L. Labuda, Issaquah, all of Wash.

[73] Assignee: NTC Technology, Inc., Wilmington, Del.

[21] Appl. No.: 598,984

[22] Filed: Oct. 17, 1990

Related U.S. Application Data

[63] Continuation-in-part of Ser. No. 528,059, May 23, 1990, abandoned.

[51] Int. Cl.$^5$ .............................................. G01N 21/61
[52] U.S. Cl. ...................... 250/343; 250/351; 250/493.1; 219/553
[58] Field of Search ............. 250/493.1, 351, 343, 250/504 R; 219/548, 553

[56] References Cited

U.S. PATENT DOCUMENTS

| | | | |
|---|---|---|---|
| 3,306,156 | 2/1967 | Glasser et al. | 250/373 |
| 3,694,624 | 9/1972 | Buchta . | |
| 3,875,413 | 4/1975 | Bridgham | 250/492.1 |
| 3,916,195 | 10/1975 | Burch et al. | 250/345 |
| 4,378,489 | 3/1983 | Chabinsky et al. | 250/493.1 |
| 4,620,104 | 10/1986 | Nordal et al. | 250/493.1 |
| 4,859,858 | 8/1989 | Knodle et al. | 250/493.1 |
| 4,859,859 | 8/1989 | Knodle et al. | 250/493.1 |
| 4,914,720 | 4/1990 | Knodle et al. | 250/343 |

OTHER PUBLICATIONS

Solomon, "A Reliable, Accurate CO$_2$ Analyzer for Medical Use", Hewlett-Packard Journal, Sep. 1981, pp. 3–11.

*Primary Examiner*—Carolyn E. Fields
*Attorney, Agent, or Firm*—Hughes, Multer & Schacht

[57] ABSTRACT

Infrared radiation emitter units for gas analyzers and other applications. The emitter has a substrate with a film of electrically resistive, emissive material on one of its surfaces. The emitter is so mounted on an emitter unit base that it can freely expand as the emitter heats up. A lead frame commutator, employed to electrically connect the emitter to an external power source, also facilitates the assembly of the unit. A component with a plated, parabolic surface collimates and focuses into an appropriate beam the energy generated by the emitter.

38 Claims, 12 Drawing Sheets

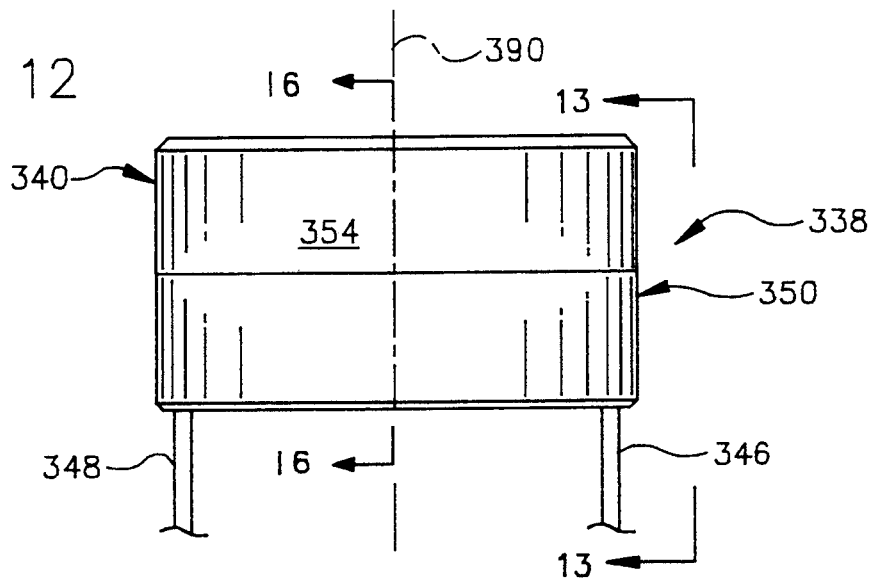
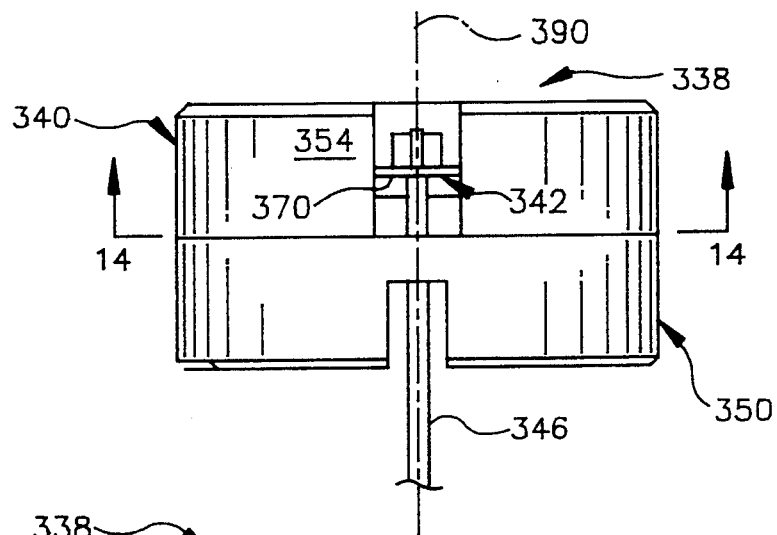
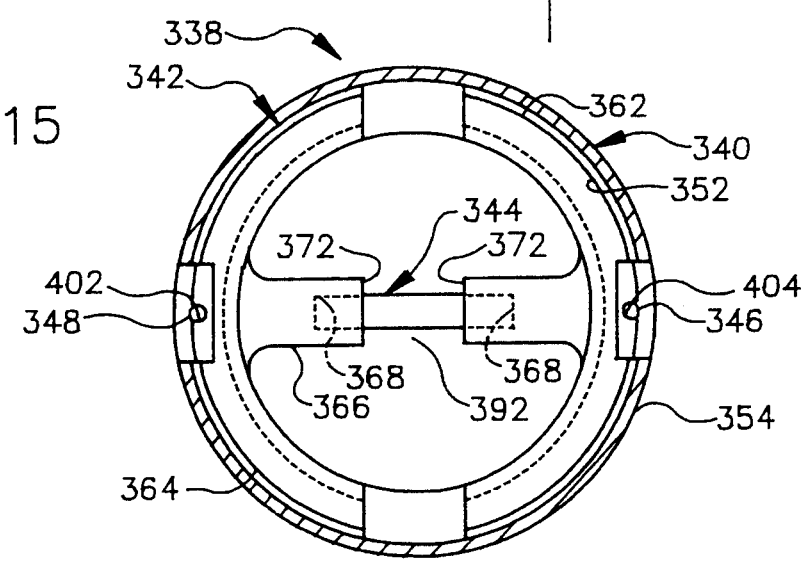

INFRARED SOURCE

RELATION TO OTHER APPLICATION

This application is a continuation-in-part of application Ser. No. 528,059 filed May 23, 1990 for DETECTORS, now abandoned.

TECHNICAL FIELD OF THE INVENTION

The present invention relates to novel, improved devices for emitting energy in the infrared part of the electromagnetic spectrum.

BACKGROUND OF THE INVENTION

U.S. Pat. Nos. 4,859,858 and 4,859,859, both entitled GAS ANALYZERS, were issued to Knodle et al. on Aug. 2, 1989. Both patents disclose state-of-the art apparatus for outputting a signal indicative of the concentration of a designated gas in a sample being monitored by the apparatus. These patents are hereby incorporated by reference thereto into this application.

The gas analyzers disclosed in the '858 and '859 patents are of the non-dispersive type. They operate on the premise that the concentration of a designated gas can be measured by: (1) passing a beam of infrared radiation through the gas, and (2) then ascertaining the attenuated level of the energy in a narrow band absorbable by the designated gas. This is done with a detector capable of generating a concentration proportional electrical output signal.

One important application of the invention at the present time is in capnometers for monitoring the level of carbon dioxide in the breath of a medical patient. This is typically done during a surgical procedure as an indication to the anesthesiologist of the patient!s condition. As the patient's well being, and even his life, is at stake, it is of paramount importance that the carbon dioxide concentration be measured with great accuracy.

In a typical instrument or system employing non-dispersive infrared radiation to measure gas concentration, including those disclosed in the '858 and '359 patents, the infrared radiation is emitted from a source and focused by a mirror on the gases being analyzed. After passing through the body of gases, the beam of infrared radiation passes through a filter. That filter absorbs all of the radiation except for that in a narrow band centered on a frequency which is absorbed by the gas of concern. This narrow band of radiation is transmitted to a detector which is capable of producing an electrical output signal proportional in magnitude to the magnitude of the infrared radiation impinging upon it. Thus, the radiation in the band passed by the filter is attenuated to an extent which is proportional to the concentration of the designated gas. The strength of the signal generated by the detector is consequently inversely proportional to the concentration of the designated gas and can be inverted to provide a signal indicative of that concentration.

While a non-dispersive analyzer must be tailored to the specific gas of interest, it is typically small, relatively cheap, and rugged enough to be used in medical and other demanding environments.

Of considerable, if not critical, importance in apparatus and systems of the character just described is the source or emitter which produces the beam of infrared radiation. In those non-dispersive gas analyzers disclosed in the '858 and '859 patents, the emitter has a substrate of a material with low thermal conductivity such as steatite. Two T-shaped conductors or terminals are bonded to the upper surface of the substrate in spaced relationship; and a film of an emissive, electrically resistive material is superimposed on the conductors and bonded to the upper surface of the substrate with its ends overlapping and electrically connected to the conductors. This emitter is attached to posts at its opposite ends and supported by those posts from a metallic emitter mount with the emissive film facing the mount. That component has a polished, parabolic, mirror surface formed in the surface which the emitter faces. This mirror collimates the emitted infrared radiation and focuses the collimated radiation into a beam directed along the optical path of the device or system in which the infrared radiation source is employed.

In the previously disclosed infrared radiation sources, the substrate bearing the emissive film was fixed at both of its ends to the supporting posts. As the substrate was heated by the emissive film, it grew or increased in length due to thermal expansion. This has led to failure of the patented type of infrared radiation source because of the stresses that were consequently imposed on the substrate and substrate-supported components.

Also, assembly of the patented infrared radiation sources is somewhat complicated and exacting. For these and other reasons, the patented sources may prove to be somewhat less than optimal in applications where a high quality, yet inexpensive, infrared radiation source is required.

SUMMARY OF THE INVENTION

We have now invented, and disclosed herein, certain new and novel infrared radiation sources which have all of the capabilities of those just described and are useful for the same purposes. However, our novel infrared radiation sources also have a number of important advantages which the patented infrared radiation sources do not have.

Briefly, the novel infrared radiation sources of the present invention are like those disclosed in the '858 and '859 patents in that they have a low thermal conductivity substrate supporting a film-type emissive element. However, they differ in one important respect in that the ends of the substrate are not fixed at an invariable distance relative to each other. Instead, one end is fixed to a lead frame, which serves as a support for the substrate-based emitter component; and the opposite end of the substrate is left free to move relative to the lead frame. Consequently, the substrate is free to grow in length as its temperature increases; and the imposition of mechanical stresses on the emitter unit is thereby avoided.

The lead frame-based approach also facilitates assembly. For example, electrical connections are easier to make (and also less apt to break); and the heretofore need for insulated leads is eliminated. Also, the film-type emissive element is automatically centered on the axis of the energy collimating and focusing mirror. This simplifies, and reduces the cost of, the assembly process by eliminating the steps heretofore employed to insure that the emissive element was accurately aligned with the collimating mirror.

Furthermore, the components of the herein disclosed infrared radiation sources are primarily molded from plastics rather than being machined from metal as in the patented sources. This allows an acceptable degree of accuracy to be maintained while significantly reducing the cost of the parts.

In addition, the novel design of the herein disclosed infrared radiation sources allows the collimating mirror to be assembled last. This minimizes the possibility that the mirrored surface might be scratched or otherwise damaged. That is important because the mirror is the most expensive part of the infrared radiation source.

Yet another, very important advantage of the infrared radiation sources disclosed herein is that the thermal, physical, electrical, and other parameters of the emissive element, the electrical conductors through which current flows to the emissive element, the substrate supporting the emissive element, and even the substrate-mounting components are so balanced and correlated that the flow of heat away from the operating emissive element is closely controlled and correlated with the emitted infrared energy. This results in an infrared radiation source which can be made to emit infrared radiation of accurately predictable intensity. This is important. For example, it is the difference in intensity between emitted and detected energy in appropriate band widths that is employed by non-dispersive gas analyzers as a measure of the concentration in a sample of the gas being monitored; and this differential is not accurate if the intensity of the emitted radiation is not.

THE PRIOR ART

Infrared radiation sources that are specifically designed for non-dispersive gas analyzers or that would appear to be useful in such equipment are disclosed in the following U.S. patents:

| U.S. Pat. No. | Patentee(s) | Issue Date |
| --- | --- | --- |
| 3,694,624 | Buchta | 26 Sep. 1972 |
| 3,875,413 | Bridgham | 01 Apr. 1975 |
| 4,378,489 | Chabinsky et al. | 29 Mar. 1983 |
| 4,620,104 | Nordal et al. | 28 Oct. 1986 |
| 4,914,720 | Knodle et al. | 03 Apr. 1990 |

Infrared radiation sources as disclosed in the foregoing patents, as well as those disclosed herein, can also be used for a variety of other purposes.

Irrespective of the end use, heretofore available infrared sources of the character disclosed in the above-cited patents have a number of drawbacks.

One is that the temperature to which such sources can be heated is often relatively low. Because the output of an infrared source is directly related to the temperature to which it is heated, the output of such sources is low; and this may make such sources impractical for many applications.

Infrared sources of the type to which the present invention relates commonly employ a heated, electrically resistive film on an appropriate substrate as an emitter of infrared radiation. This unit has heretofore been fixed at its opposite ends to a suitable support so that the necessary electrical connections to the emissive layer can conveniently be made. As discussed above, such infrared radiation sources frequently fail.

OBJECTS OF THE INVENTION

From the foregoing, it will be apparent to the reader that one important and primary object of the present invention resides in the provision of novel, improved sources or emitters of infrared radiation.

Other also important but more specific objects of the present invention reside in the provision of infrared radiation sources:

which are unlikely to fail because of the thermally induced growth of a substrate supporting the emissive element of the device;

which have a construction such that the emissive element of the device is automatically aligned in the course of assembling the device with a mirror employed in the device to collimate and focus the emitted radiation;

which facilitate the making of electrical connections and eliminate the requirement that insulated wire be employed for this purpose;

which are made up of parts that can be inexpensively yet accurately fabricated and easily assembled;

which can be assembled in a manner that protects the most expensive part of the device—a collimating and focusing mirror—from damage by allowing it to be assembled last;

which are capable of emitting infrared radiation of accurately predictable intensity.

Still another important and primary object of the invention resides in the provision of novel methods for assembling an infrared radiation source or emitter unit of the character identified in the preceding objects.

Still other important objects and features ant additional advantages of the invention will be apparent to the reader from the foregoing and the appended claims and as the ensuing detailed description and discussion proceeds in conjunction with the accompanying drawings.

BRIEF DESCRIPTION OF THE DRAWINGS

In the drawings:

FIG. 12 is an elevation of a second infrared radiation source also embodying the principles of the present invention;

FIG. 13 is a second elevation of the source shown in FIG. 12, in this case looking in the direction indicated by arrows 13—13 in FIG. 12;

FIG. 15 is a section through the source of FIG. 12, taken substantially along line 15—15 of FIG. 16;

DETAILED DESCRIPTION OF THE INVENTION

Figure 1:
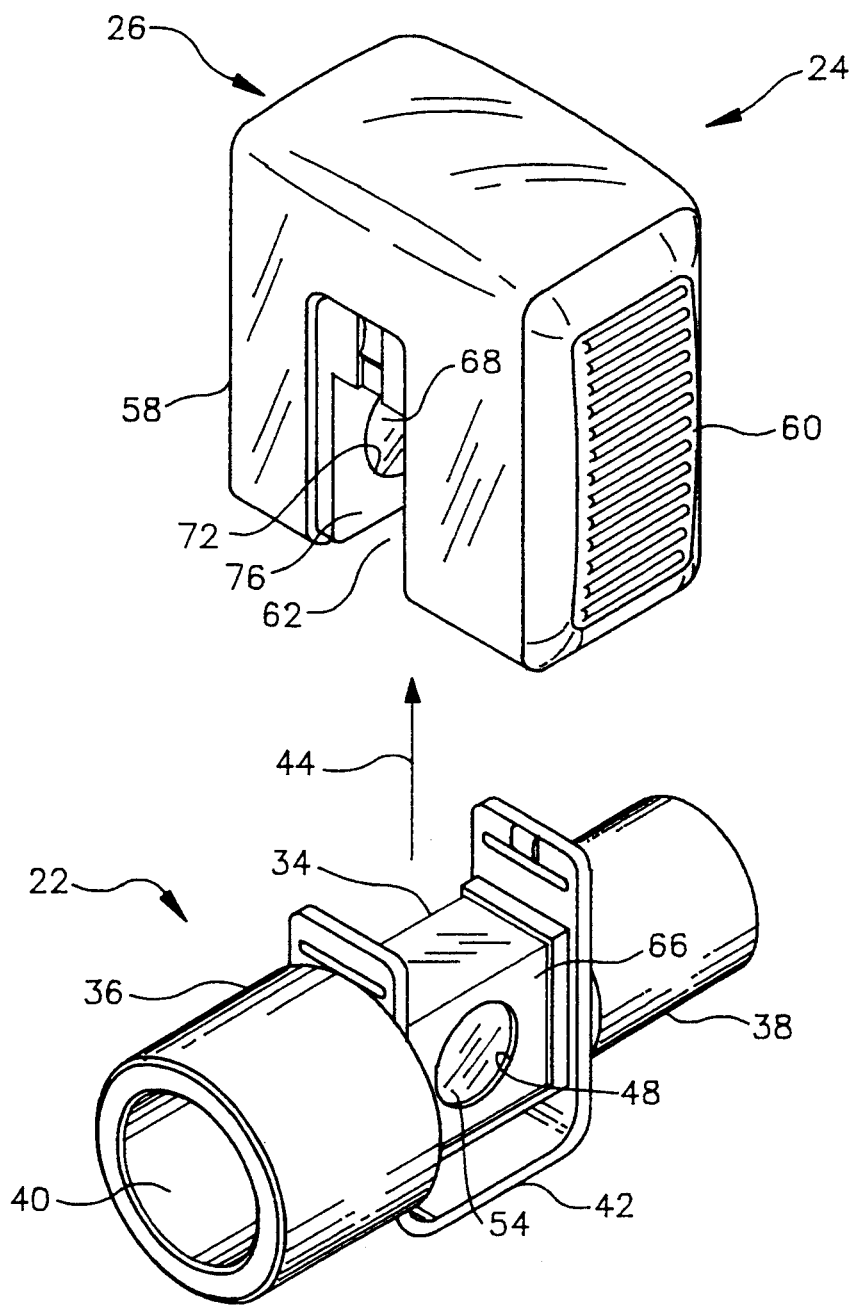
FIG. 1 is an exploded view of: (a) an airway adapter which provides a particularized flow path for a gas being analyzed, and (b) a transducer which outputs a signal indicative of the concentration of the designated gas in the mixture and a reference signal; that transducer includes an infrared radiation source or emitter unit constructed in accord with the principles of the present invention.

The principles of the present invention can be employed to particular advantage in transducers for outputting: (a) a signal proportional in magnitude to the concentration of carbon dioxide flowing through an airway adapter in a patient-to-mechanical ventilator circuit, and (b) a reference signal. These signals can be ratioed in the manner disclosed in above-incorporated U.S. Pat. Nos. 4,859,858, and 4,859,859 to provide a third signal accurately and dynamically representing the concentration of the carbon dioxide flowing through the airway adapter. A representative and preferred airway adapter and a complementary transducer constructed in accord with, and embodying, the principles of the present invention are shown in FIGS. 1 and 2 and respectively identified by reference characters 22 and 24.

Figure 2:
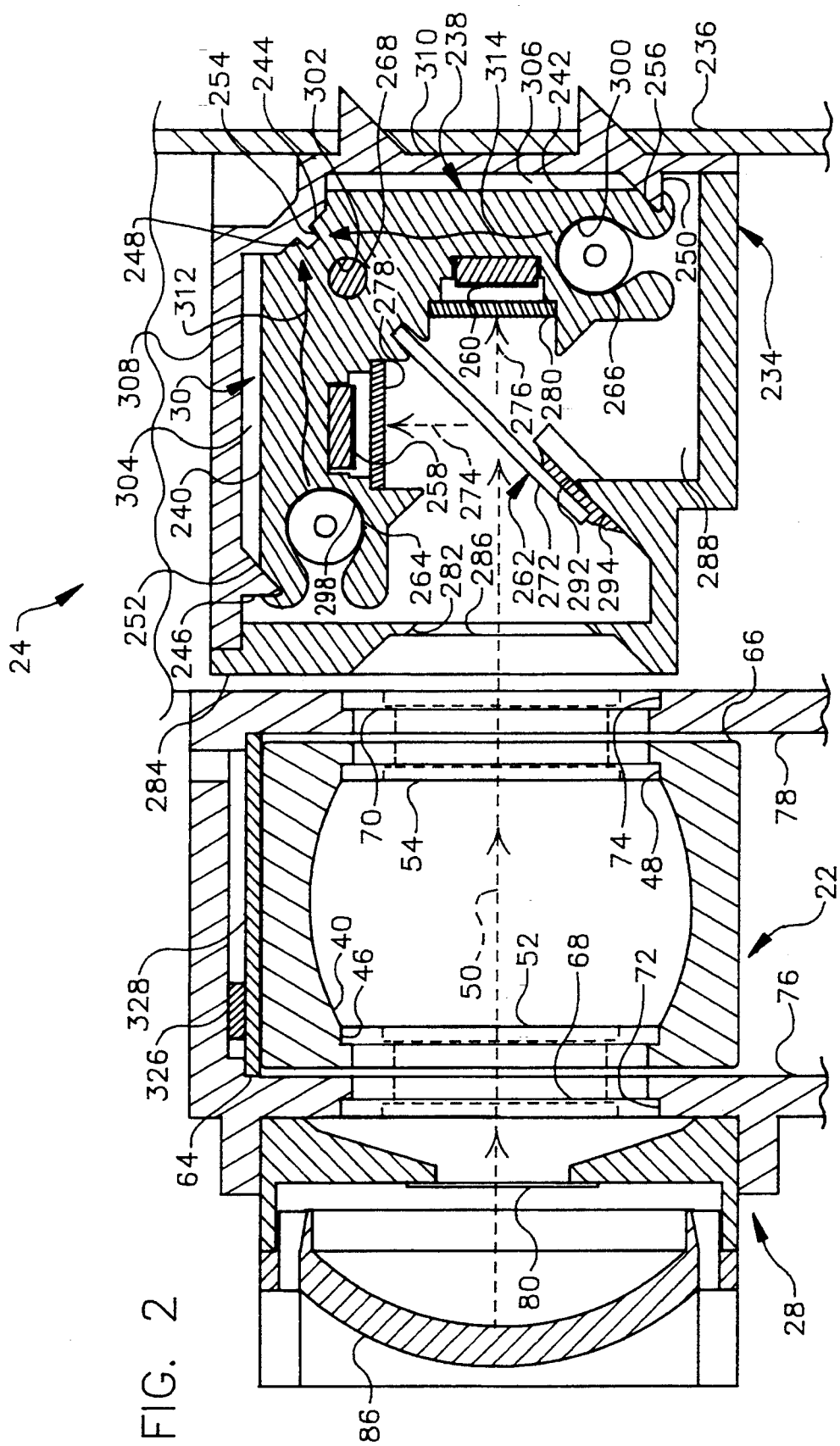
FIG. 2 is a section through, and depicts, a detector-incorporating optical system of the airway adapter/transducer assembly.

FIG. 1 shows primarily the polymeric housing 26 of transducer 24. This transducer also includes: (a) an infrared radiation emitter unit 28 (FIGS. 1-10); (b) a detector unit 30 (FIG. 2); and (c) a detector unit power supply 32.

The illustrated airway adapter 22 is designed for connection between an endotracheal tube inserted in a patient's trachea and the plumbing of a mechanical ventilator, and transducer 24 is in this instance employed to measure the expired carbon dioxide level of a medical patient.

The particular airway adapter 22 illustrated in FIG. 1 is not, by itself, part of the present invention. Consequently, it will be described herein only to the extent necessary for an understanding of the present invention.

Figure 4:
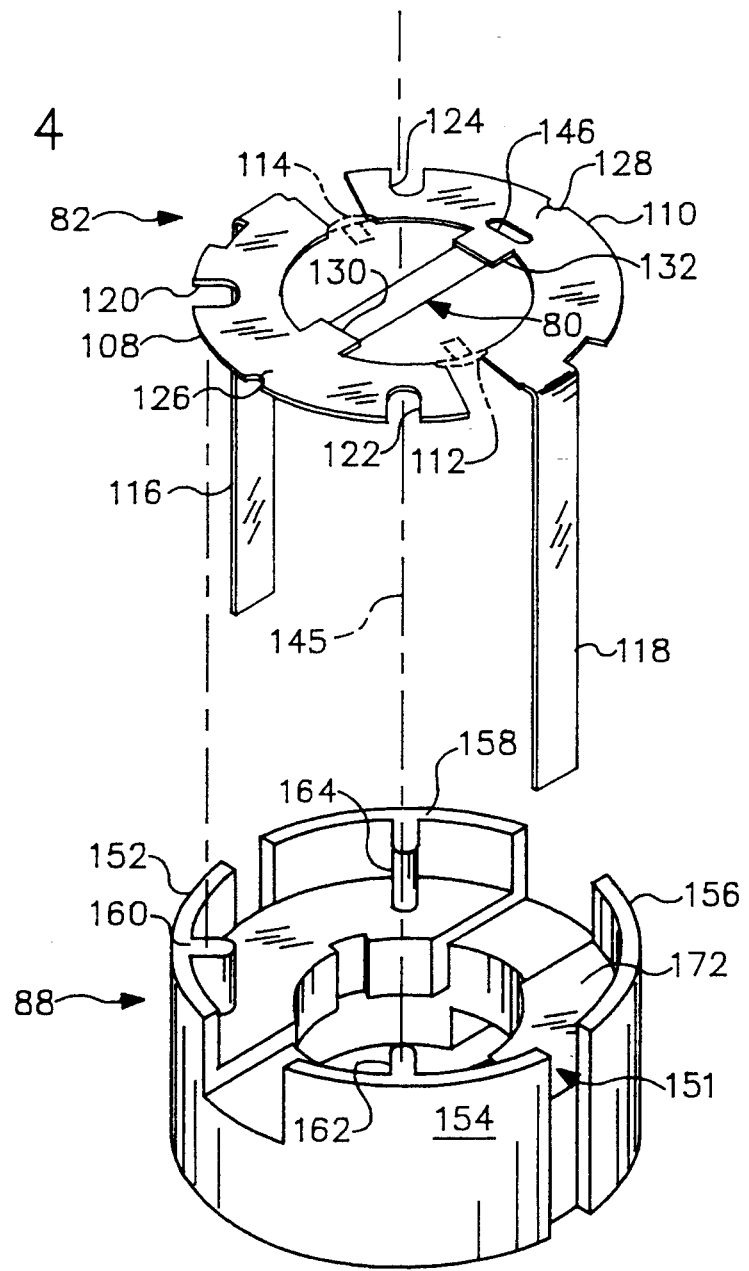
FIG. 4 is a second exploded view presented to show the relationship between: (a) a lead frame employed in the device to support the infrared radiation emitting element and to make electrical connections to that unit, and (b) a molded ring which supports the lead frame and is the base of the device.

Referring then to FIGS. 1 and 4, airway adapter 22 is a one-piece unit typically molded from Valox polyester or a comparable polymer. Airway adapter 22 has a generally parallelepipedal center section 34 and two cylindrical end sections 36 and 38 with a sampling passage 40 extending from end-to-end through the adapter. End sections 36 and 38 are axially aligned with center section 34.

The central section 34 of airway adapter 22 provides a seat for transducer 24. An integral, U-shaped casing element 42 positively locates transducer 24 endwise of the adapter and, also, in that transverse direction indicated by arrow 44 in FIG. 1. That arrow also shows the direction in which airway adapter 22 is displaced to assemble it to transducer 24.

Apertures 46 and 48 are formed in the center section 34 of airway adapter 22. With transducer 24 assembled to the airway adapter, these apertures are aligned along an optical path identified by reference character 50 in FIG. 2. That optical path extends from the infrared radiation emitter unit 28 in transducer 24 transversely across airway adapter 22 and the gas(es) flowing therethrough to the infrared radiation detector unit 30 of transducer 24.

To: (a) keep the gases flowing through airway adapter 22 from escaping through apertures 46 and 48 without attenuating the infrared radiation traversing optical path 50, and (b) keep foreign material from the interior of the airway adapter, the apertures are sealed by sapphire windows 52 and 54. Sapphire windows are employed because other materials such as glass or plastic would absorb the infrared radiation to an extent that would significantly degrade the quality of the signals generated in detector unit 30.

That casing 26 of transducer 24 in which the source unit 28 and detector unit 30 are housed has first and second end sections 58 and 60 with a rectangularly configured gap 62 therebetween. With the transducer assembled to airway adapter 22, the two sections 58 and 60 of transducer casing 26 embrace those two inner side walls 64 and 66 of airway adapter central section 34 in which energy transmitting windows 52 and 54 are installed.

Optically transparent windows 68 and 70 are installed along optical path 50 in apertures 72 and 74 provided in the inner end walls 76 and 78 of transducer housing 26. These windows allow the beam of infrared radiation generated in unit 28 in the left-hand end section 58 of transducer housing 26 to pass airway adapter 22 and from the airway adapter to the detector unit 30 in the right-hand section 60 of the transducer housing. At the same time, windows 68 and 70 keep foreign material from penetrating to the interior of the transducer casing.

Referring now to FIGS. 3-10, the unit 28 employed to emit infrared radiation, to form that energy into a beam, and to propagate the beam along optical path 50 includes: an infrared radiation emitter 80, a lead frame 82, a tube or cap 84, and a mirror component 86, all supported from a base 88.

Figure 5:
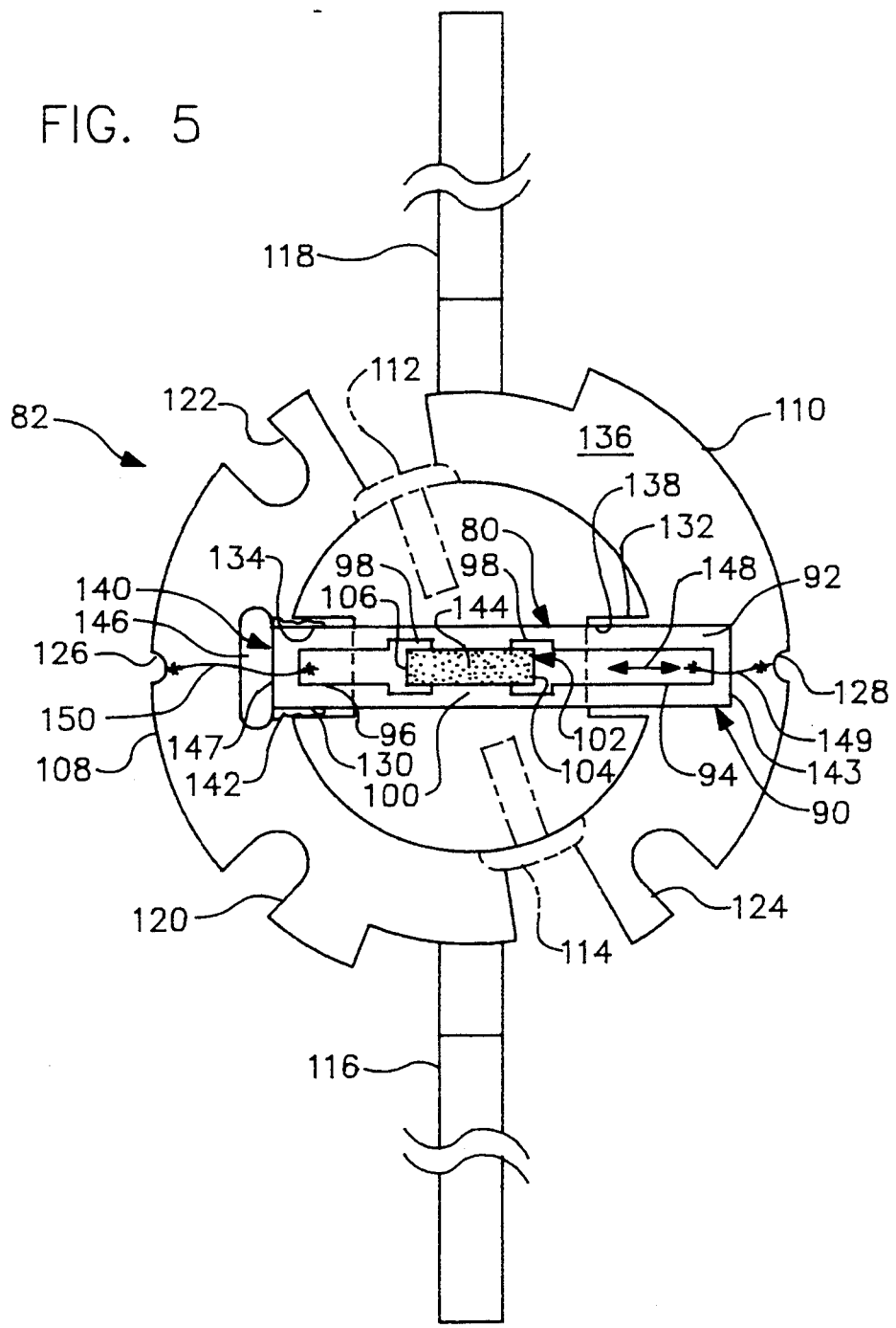
FIG. 5 is a plan view, prior to its being installed in the base, of an assembly made up of the infrared radiation emitter unit and the supporting lead frame.
Figure 6:
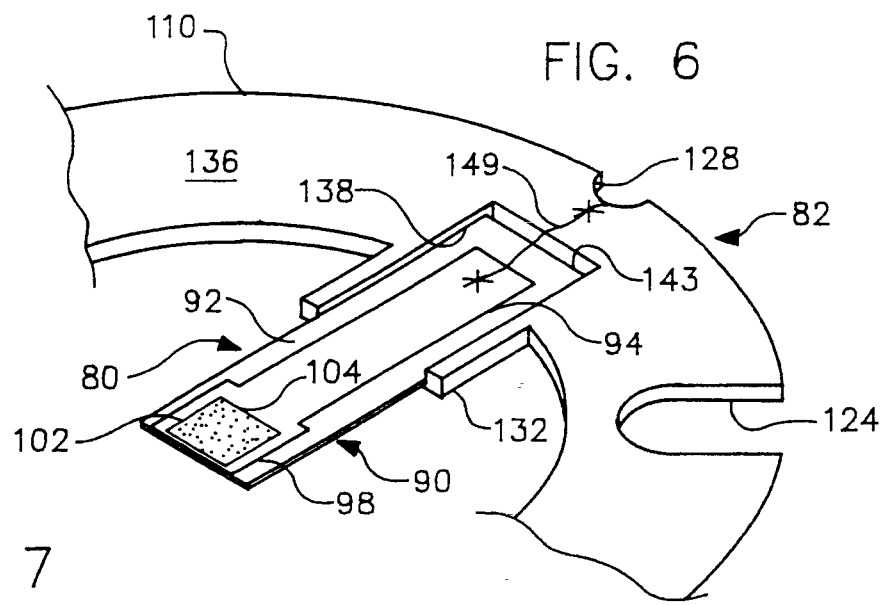
FIG. 6 is a fragmentary, pictorial view of the emitter unit/lead frame assembly; this figure shows a novel floating relationship between the emitter unit and the lead frame which allows the emitter to freely grow in length as the emitter unit temperature increases, thereby eliminating the imposition of stresses which might damage the emitter unit or electrical connections to that unit.
Figure 7:
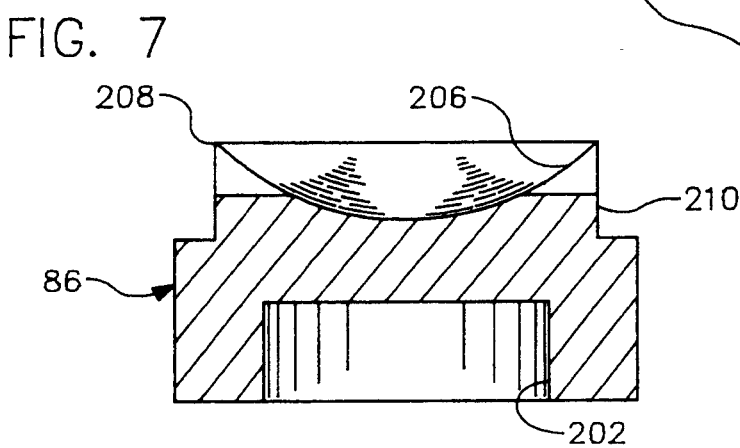
FIG. 7 is a vertical section through a parabolic mirror component employed in the infrared radiation source to collimate, focus into a beam, and direct along a specific optical path infrared radiation outputted by the emitter unit.

Infrared emitter or energy source 80, best shown in FIGS. 5 and 6, is of a unique thick film construction. It includes a substrate 90 which, in one actual embodiment of the invention, is 0.250 inch long, 0.040 inch wide, and 0.005 inch thick. This substrate can however range in thickness from 0.003 to 0.005 in., and it is formed from a material having low thermal conductivity. Steatite (a polycrystalline material containing magnesium oxide and silicon dioxide) is preferred because it has a thermal conductivity which is on the order of one magnitude less than conventional low thermal conductivity materials such as alumina. This is important because it significantly reduces the power required to heat the emitter to its operating temperature.

However, alumina can be employed instead of steatite. It if is, the substrate is preferably coated with a film of a dielectric material having low thermal conductivity such as a dielectric glass.

Another substrate material that can be employed is fused silica.

Bonded to the upper surface 92 of substrate 90 are two T-shaped electrical conductors or terminals 94 and 96. In the exemplary infrared radiation emitter 80 illustrated in FIGS. 5 and 6, the head 98 of each conductor is 0.035 inch long; and the gap 100 between the conductors is 0.030 inch.

Terminals 94 and 96 are preferably formed of a platinum and gold containing cermet obtained by printing an ink such as DuPont's 4956 on the surface 92 of substrate 90 and then firing the substrate.

Superimposed on terminals 94 and 96 and bonded to the upper surface 92 of substrate 90 with its ends overlapping conductors 94 and 96 is a thick film or layer 102 of an emissive, electrically resistive material. The preferred material is obtained by firing Electro-Science Labs ESL3812 Ink. This ink contains a major proportion of platinum and has an operating temperature in the range of 250–300 degrees centigrade.

The illustrated, exemplary, emissive layer 102 is 0.070 inch long; and the two ends 104 and 106 of the emitter overlap 0.020 inch onto the conductor 94 and the conductor 96 of emitter 80. Thus, the total overlap constitutes 57 percent of the total area of emissive layer 102. This is within the preferred and operable range of 50 to 60 percent.

Overlaps in the range just described tend to keep the current density at the interfaces between emissive layer 102 and conductors 94 and 96 from becoming too high and causing emitter 80 to fail by burnthrough or fatigue cracking of the emissive layer.

That we can thus prevent failures of emitter 80 is surprising. Heretofore, it has been believed that successful performance of a thick film device with an active layer-to-conductor overlap could not be obtained with an overlap exceeding about 15 percent.

Also contributing to the resistance to failure from exposure to excessive current densities is the T-shaped configuration of conductors 94 and 96. This is at least potentially superior to the more conventional rectangular or straight sided conductors as far as resistance to emissive layer burnthrough is concerned.

It is one of the important features of the present invention that the emissive layer 102 and substrate 90 of emitter 80 are so constructed and related as to optimize the performance of the emitter as the emissive layer is periodically heated to produce the wanted emission of radiant energy. This important result is obtained by so correlating the dimensions and thermal conductivities of the emissive layer and substrate with the duty cycle of power supply as to satisfy the equation:

$$T(t) = \begin{cases} P_p\{R_{TI}[d + (1-d)(1 - e^{-t/\tau_I})] + R_{TII}[d + (1-d)(1 - e^{-t/\tau_{II}})] + \\ R_{TIII}[d + (1-d)(1 - e^{-t/\tau_{III}})]\} + T_o, \text{ for } 0 \leq t \leq t_d \\ P_p\{R_{TI}[d + (1-d)(1 - e^{-t_i/\tau_I})e^{-t_d/\tau_I}] + R_{TII}[d + (1-d)(1 - e^{-t_i/\tau_I})e^{-t_d/\tau_I}] + \\ R_{TIII}[d + (1-d)(1 - e^{-t_i/\tau_I})e^{-t_d/\tau_I}]\} + T_o, \text{ for } t_d < t \leq t_p \end{cases}$$

for $t_d < t \leq t_p$ where $t_i = t - t_d$, where:
A = cross sectional area of a layer perpendicular to the major heat flow;
L = thickness of the layer parallel to the direction of major heat flow;
$\rho$ = (rho) density of the layer material;
c = specific heat of the layer material;
k = thermal conductivity of the layer material;
$R_T$ = 'Thermal Resistance' of the layer, where $R_T = L/Ak$. $R_{TI}$, $R_{TII}$ and $R_{TIII}$ are the thermal resistances for layers I, II and III respectively;
$C_T$ = 'Thermal Capacitance' of the layer;
$I_T$ = 'Thermal Current' or heat flow;
$V_T$ = 61 Thermal Voltage' or temperature;
$\tau$ = 'Thermal Time Constant' of the layer, where $\tau = R_T C_T$ for each layer I, II and III;
Heat flow equation: $V_T(t) = R_T I_T(t) \exp(-t/\tau)$;
$T_o$ = ambient temperature of the back surface of the layer;
T(x) = temperature as a function of location in the layer ($0 \leq X \leq L$);
$P_p$ = peak electrical power applied to the thick film resistor;
$P_{ave}$ = average electrical power applied to the thick film resistor;
g(t) = general on-off pulsing function;
$t_d$ = time the pulse voltage is ON;
$t_p$ = period of the pulsing wave form;
$t_i = T - T_d$ when $t_d < t \leq t_p$;
d = duty cycle of the pulsing waveform, where $d = t_d/t_p$.

In the model $V_T(t) = R_T I_T(t) \exp(-t/\tau)$ is replaced by $$T(x,t)\begin{bmatrix} = R_T[P_{ave} + (P_p - P_{ave})g(t)] \\ x = 0. \end{bmatrix} = P_p R_T[d + (1-d)g(t)]$$

As will be apparent to the reader from the foregoing model, the following are the critical parameters of an emitter of the character disclosed herein:

| Emissive Element | Density $\rho$ |
| --- | --- |
| | Specific Heat C |
| | Thermal Conductivity k |
| | Thickness L |
| Substrate | Density $\rho$ |
| | Specific Heat C |
| | Thermal Conductivity k |
| | Thickness L |

The thermal model also makes it clear that the various parameters of the emissive element, as well as those of the substrate, have to be balanced to obtain an emitter that will emit infrared energy of predictable varying intensity. This variation is controlled by the voltage across the source.

The majority of the energy generated by the dissipation of the power through the resistor is conducted away from the resistor through that component and the substrate of the emitter in the form of thermal energy or heat. The rate at which this heat is conducted away from the emissive element or resistor is controlled by the physical parameters of the resistor, conductor, substrate and mounting assemblies.

Also important to the performance of the emitter is the emissivity of the resistor surface. It does no good to modulate the heat of the resistor surface if that resistor surface is inefficient in radiating the concomitant infrared energy.

The emissivity and resulting emission of infrared energy (heat) from the resistor is negligible in terms of the total heat flow of the system, but it is quite important in the functioning of the resistor assembly as an efficient infrared radiation emitter.

Thus, the total assembly of emitter components must be considered when modeling the heat flow since the resistor and conductors, as well as the substrate material, are all within one order of magnitude for all parameters. Consequently, changes in the thicknesses, when all other parameters are held constant, will significantly affect the temperature excursions. These effects are seen both analytically and experimentally.

Nevertheless, changing the substrate thickness from 0.003" to 0.005" with correlated changes in other emitter components did not unacceptably affect the thermal performance of the emitter. This is significant in that the thicker substrate makes a more rugged emitter which is less susceptible to breakage.

It has of course been found, as predicted by the thermal model, that the emissive element thickness for a given resistance must be tightly controlled to obtain satisfactory performance. This is because the thermal conductivity of the emissive layer is much higher than that of the substrate. Since the emissive layer thickness is only about one-fourth to one-fifth that of the substrate, small variations in the emissive element thickness have large effects on the thermal performance.

One important item that can be determined from the model is the wave shape of the emitted infrared radiation for a defined set of physical parameters. This is important because of the time and other savings that can be realized by not having to build and evaluate large numbers of prototypes. That is, the performance of an emitter is tied directly to the wave shape of the emitted energy. Consequently, one can use the thermal model to evaluate different sets of selected parameters without actually building and testing emitters with those parameters.

Other important items of information can also be readily derived from the thermal model. As an example, one gas analyzer system with an infrared radiation emitter of the character defined by the thermal model requires at least a 16 volt drive at 48 Hz with a 10% duty cycle to provide sufficient emitter output for the system to function to specification. If the substrate material of the emitter were to be changed from steatite to alumina, the voltage would have to be increased to over 21 volts to obtain comparable performance. However, at this higher voltage, the resistor material breaks down due to overheating. Thermal effects such as these can be modeled and materials chosen that will allow for as high a peak temperature with as much modulation of the temperature and as low a dissipated power as possible.

Other criteria that are important in designing an infrared emitter of the character disclosed herein are the frequency and duty cycle of the electrical power source employed to drive the emitter. By using the thermal model to compare the differences between two different emitter outputs from similar resistors driven with different pulse streams, one can more easily determine optimum driving conditions.

Previously proposed mathematical models for infrared radiation sources which fail to take the electrically resistive, emissive layer into account, such as that disclosed in U.S. Pat. No. 4,620,104 issued Oct. 28, 1986 to Nordal, are woefully inadequate. The emissive layer will typically comprise 25 percent of the thickness of the infrared radiation emitter. The effect of that component can therefore not be neglected, as heretofore been done, with any expectation that a mathematical model will accurately reflect the actual operation of the infrared radiation source.

Referring now more specifically to FIGS. 3–6, lead frame 82 is stamped from a sheet of conductive metal such as tin plated copper. The lead frame has two, generally similar, arcuate segments 108 and 110 connected by integral tabs 112 and 114, a conductor or terminal 116 integral with and extending radially from segment 108, and a second conductor or terminal 118 which is integral with and extends radially from lead frame segment 110 in the opposite direction at a location halfway around the circumference of the lead frame from terminal 116.

As just indicated, each of the two lead frame segments 108 and 110 has a generally arcuate configuration. U-shaped alignment slots 120 and 122 open onto the periphery of segment 108, and a third, U-shaped alignment slot 124 opens onto the periphery of segment 110. Also opening onto the peripheries of lead frame segments 108 and 110, respectively, are conductor receiving slots 126 and 128.

Additionally found in lead frame 82 are emitter supports 130 and 132. Support 130 is integral with and extends radially inward from, lead frame segment 108. Emitter support 132 is axially aligned with support 130. It is integral with, and extends radially inward from, lead frame segment 108. Emitter support 130 has an emitter receiving recess 134 on what will hereinafter be referred to as the bottom side 136 of lead frame 82; and a second emitter receiving recess 138 is formed in emitter support 132, also on the bottom side 136 of lead frame 82.

One end 140 of emitter 80 is seated in emitter support recess 134 and bonded in place as by the illustrated epoxy adhesive 142. By way of surface tension, the epoxy adhesive draws emitter 80 into the position illustrated in FIG. 5. This locates the midpoint 144 of emitter 102 on the centerline 145 of emitter unit 28. This is important in that it optimizes the ability of mirror assembly 86 to collimate and focus the energy emitted from the thick film or layer 102; and this results in an optical beam of optimum quality being projected from emitter unit 28.

In particular, and as shown in FIG. 5, there is an elongated, transversely oriented slot 146 in lead frame segment 108 at the left-hand end of emitter receiving groove or recess 138. Because of slot 146, the epoxy adhesive 142 will not flow past the boundary identified by reference character 147 in FIG. 5. Consequently, the left-hand, fixed end 140 of emitter 82 is drawn even with, but not beyond, boundary 147. With end 140 of the emitter so located, the emitter is precisely centered on the longitudinal centerline 145 of unit 28.

The opposite end 143 of the emitter is seated in the slot 138 in emitter support 132. However, emitter 80 is not bonded to that support but is, instead, free to move back and forth in the slot as indicated by arrow 148 in FIGS. 5 and 6. As a consequence, when current is supplied across the emissive layer 102 of emitter 80, heating up the emissive layer and substrate 90, the substrate grows or increases in length due to thermal expansion; but this growth is accommodated rather than being constrained. As a consequence, the stresses which would be imposed upon emitter 80 if both ends were fixed are avoided, eliminating the damage to emitter 80 or complete failure of that component which might result if mechanical stresses were imposed upon it.

After emitter 80 has been assembled to lead frame 82, the two terminals 94 and 96 are respectively connected to conductive segments 108 and 110 of the lead frame 82. Electrical conductors or leads soldered at opposite ends to the emitter unit terminals 94 and 96 and lead frame segments 108 and 110 are employed for this purpose. They are illustrated in FIG. 5 and identified by reference characters 149 and 150.

Figure 3:
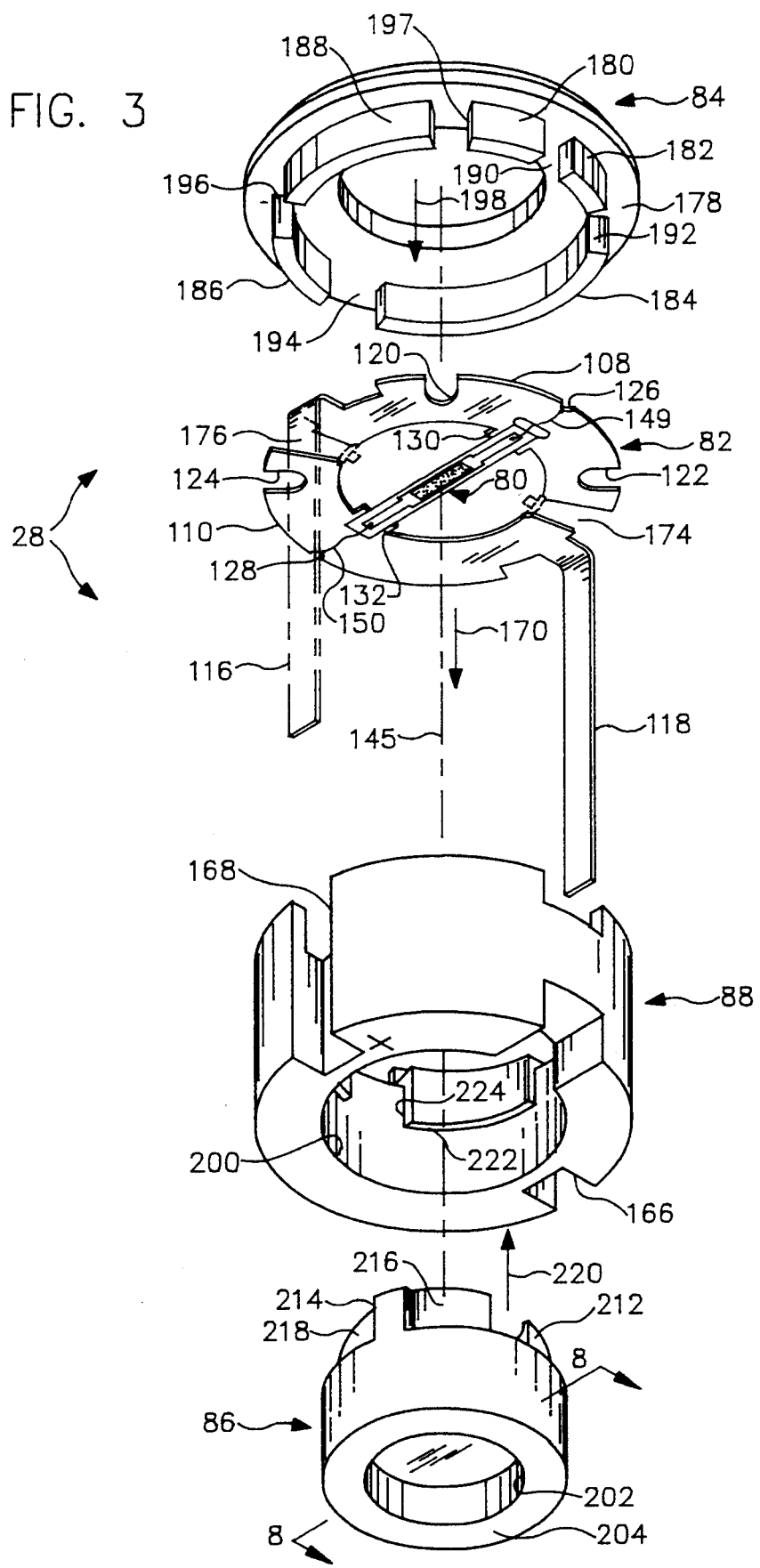
FIG. 3 is an exploded view of the infrared radiation source.

Once the steps just discussed have been completed, lead frame terminals 116 and 118 are bent at right angles to the conductor segments 108 and 110 of the lead frame, and the emitter or lead frame assembly is then installed in the base 88 of radiant energy emitting unit 28. This component, best shown in FIGS. 3 and 4, is a monolithic member. The environment in which this component operates can reach an elevated temperature due to heating by the emissive layer 102 of emitter 80. The base is therefore fabricated of a polysulfone or comparable polymer which will remain structurally stable at the temperatures it reaches during the operation of emitter unit 28 and as leads 149 and 150 are soldered to base-supported lead frame segments 108 and 110.

Base 88 has a cylindrical configuration; a platform 151; and integral, annular wall segments 152 . . . 158 which extend upwardly from platform 151 with base 88 in the orientation shown in FIG. 4. Extending inwardly from each of wall segments 152, 154, and 158 is a boss 160, 162, or 164 configured to complement a corresponding one of the three U-shaped slots 120, 122, and 124 in the segments 108 and 110 of lead frame 82. Diametrically opposed slots 166 and 168 are formed in, and extend from the top to the bottom of, base 88. These slots open onto the exterior of the base, are slightly wider than the terminals 116 and 118 of lead frame 82, and are slightly deeper than the lead frame terminals. Consequently, the terminals 116 and 118 may be fitted within slots 166 and 168 when emitter unit 28 is assembled.

The assembly of emitter 80 and lead frame 82 is installed in base 88 by aligning it relative to the base as shown in FIG. 4 and then displacing the emitter/lead frame assembly downwardly in the direction indicated by arrow 170 until the segments 108 and 110 of the lead frame are seated on the upper surface 172 of base platform 151.

The radial bosses 160 . . . 164 of base 88 guide lead frame 82 relative to base 88 as the lead frame/emitter assembly is installed, then and thereafter maintaining the wanted relationship between the assembly and base. Once lead frame segments 108 and 110 are seated on the platform 151 of base 88, the emitter/lead frame assembly is retained in place by an appropriate adhesive (not shown) between the lead frame segments and the upper surface 172 of the platform.

As is apparent from FIGS. 3 and 4, there is an asymmetrical relationship of the radially oriented lugs or bosses 160 . . . 164 on base 88 and the complementary notches 120 . . . 124 of lead frame 82. This is an important feature of the present invention, as far as the just-discussed installation of the emitter/lead frame assembly is concerned, because it keeps the lead frame from being installed upside down in base 88.

After the emitter/lead frame assembly is installed and bonded to base 88, the two lead frame tabs 112 and 114 are removed, leaving gaps 174 and 176 between the lead frame segments 108 and 110. This electrically isolates lead frame segment 108 from segment 110. Therefore, current supplied to one of the lead frame terminals 116 and 118 flows from the associated lead frame segment 108 or 110 through emitter 80 and the second lead frame segment to the second of the two lead frame terminals. For example, current applied to terminal 116 flows seriatim through: lead frame segment 108, lead 149, emitter terminal 94, emissive layer 102, emitter terminal 96, lead 150, and lead frame segment 110 to lead frame terminal 118. This results in emissive layer 102 being heated and emitting the wanted energy in the infrared portion of the-electromagnetic spectrum.

The provision of the breakaway tabs 112 and 114 just discussed is an important feature of the present invention from the viewpoint of assembling emitter unit 28. The assembly of emitter 80 and lead frame 82 is quite fragile as are the connections from leads 149 and 150 to emitter terminals 94 and 96 and lead frame segments 108 and 110. The assembly would be difficult to handle, install, and align if lead frame segments 108 and 110 were separate components. With lead frame segments 108 and 110 integrated, however, this ceases to be a problem because the lead frame acts as a supporting frame as well as an assembly jig. Handling and installation are very much simplified, especially as the removal of tabs 112 and 114 subsequent to the installation of the emitter/lead frame assembly is easily accomplished.

From another viewpoint, an emitter/lead frame assembly with separate lead frame segments would require a special and relatively difficult to use fixture to install; and, even then, handling of this fragile assembly would pose a problem. In contrast, by employing the unitary lead frame with its breakaway tabs, the lead frame can be made to serve as an integral, assembly fixture for the emitter and lead frame.

Once the emitter/lead frame assembly has been installed in and bonded to base 88 and tabs 112 and 114 removed, emitter unit tube or cap 84 is installed. This component, shown in FIGS. 3 and 8-10, is an annular member fabricated from a polymer with a high degree of structural stability such as acrylonitrile-butadiene-styrene (ABS).

Cap 84 is of the same diameter as base 88. It has a flat platform 178 from which a circular array of annular bosses 180 . . . 188 separated by gaps 190 . . . 197 depend.

Cap 84 is installed by displacing it relative to base 88 in the direction indicated by arrow 198 in FIG. 3, once the cap has been oriented relative to the base as shown in that figure. As this movement continues, the annular wall segments 152 . . . 158 of base 88 ride up through the slots or gaps 190 ... 197 in cap 84 until the platform 178 of the cap is seated on the upper ends of the annular walls segments.

An appropriate, but unillustrated, adhesive is employed to secure cap 84 to base 88.

With cap 84 installed, the gaps 190 and 194 between depending, annular segments 152, 154, 158, and 160 are aligned with the external slots or recesses 126 and 128 in base 88. This accommodates the two terminals 116 and 118 of lead frame 82 in cap 84.

The remaining step in putting together emitter unit 28 is to install mirror component or assembly 86 in base 88.

The mirror assembly, best shown in FIGS. 3, 7, 9, and 10, is a monolithic member with a circular cross section. The mirror assembly, also typically fabricated from ABS, is dimensioned to fit within the circular central bore 200 of emitter base 88. A circular recess 202 is formed in mirror assembly 86, and that recess opens onto the bottom side 204 of the mirror assembly. A second, parabolic surface 206 is formed in the opposite, upper side 208 of the assembly. Parabolic surface 206 is first plated with a typically 2 mil thick coating of copper and then over-plated with gold, the thickness of the gold layer typically being in the range of 2 $\mu$in. This provides a parabolic mirror for collimating and focusing the infrared radiation from emitter 80.

As is best shown in FIG. 3, the upper part 210 of mirror assembly 86 is stepped inwardly, leaving a pair of longitudinally extending, diametrically opposed lugs 212 and 214. The upper part 210 of the mirror assembly is cut away, leaving diametrically opposed, longitudinally extending grooves 216 and 218 with locations 90° removed from lugs 212 and 214.

Mirror assembly 86 is installed in base 88 with its axis of symmetry coinciding with emitter unit longitudinal centerline 145. This is accomplished by moving the mirror assembly relative to the base as indicated by arrow 220 in FIG. 3. As this displacement continues, the just-described lugs and grooves 212 ... 218 interact with corresponding, integral, longitudinally extending lugs 222 (only one of which is shown) and grooves 224 in base 88 to guide the mirror assembly relative to the base. As in the case of cap 84, an appropriate but not illustrated adhesive can be employed to hold the mirror assembly in place.

Figure 10:
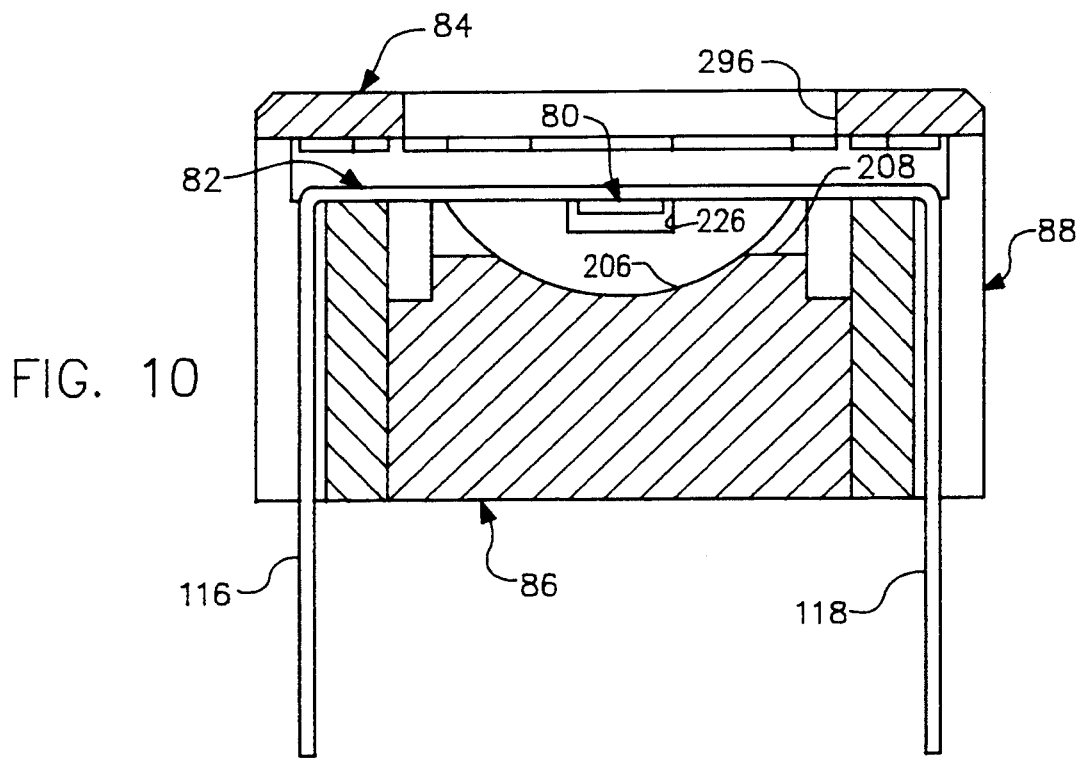
FIGS. 9 and 10 are sections through the device taken essentially along lines 9—9 and 10—10 of FIG. 8.
Figure 8:
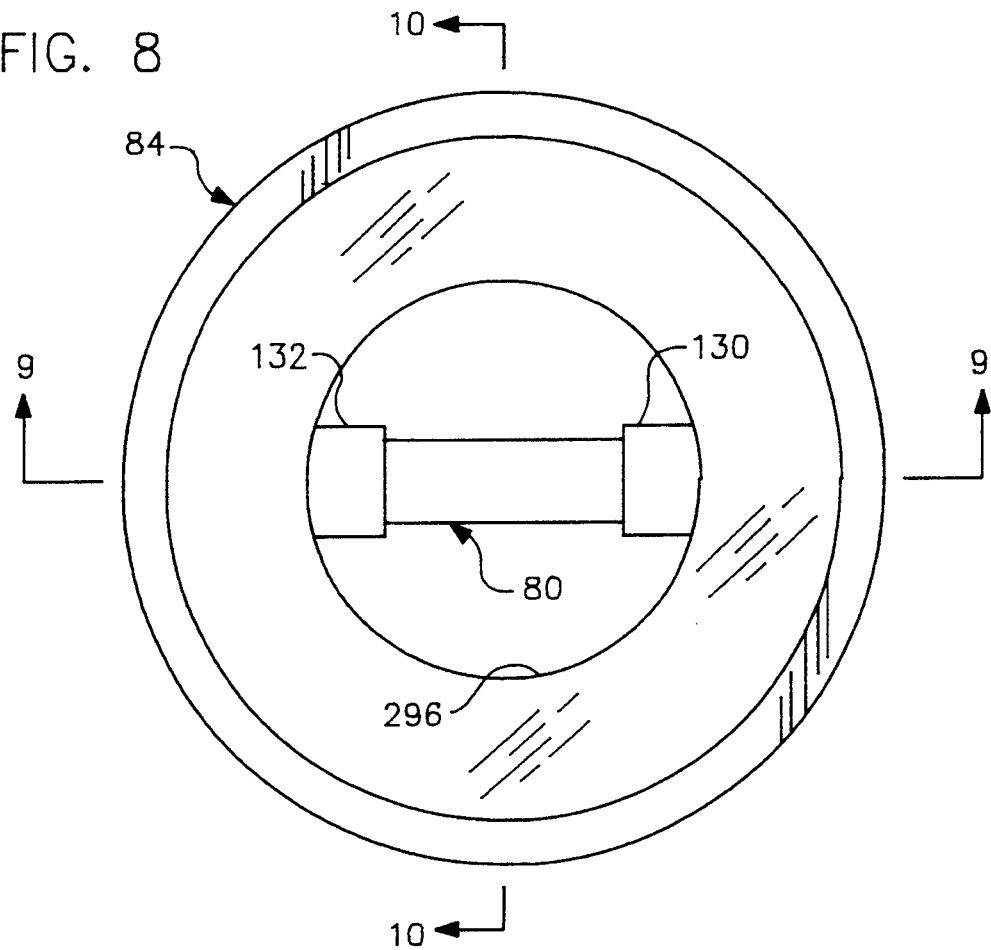
FIG. 8 is a plan view of the assembled source or device.
Figure 9:
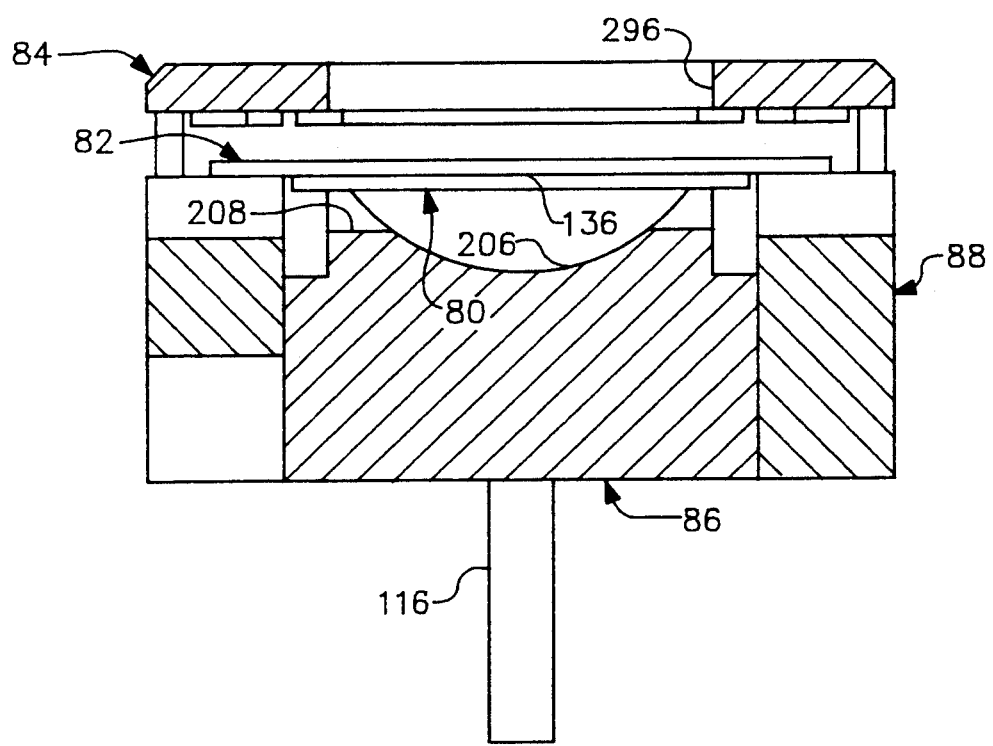

As shown in FIG. 10, there is a notch 226 in the upper end of mirror component 86. This separates emitter 80 from the upper side 208 of the mirror component 86, eliminating the possibility of damage to the emitter or to the mirror-providing plating on the parabolic surface 206 of the mirror component.

Generation of a detector output signal of a high enough signal-to-noise ratio to be useful requires that the beam of attenuated infrared radiation falling on the detector be modulated. It was pointed out in U.S. Pat. Nos. 4,859,859 and 4,859,858 this can be done by applying electrical pulse to the electrically resistive, emissive component of a thick film infrared radiation source. One system for supplying such pulses is shown in FIG. 11 and identified by reference character 228.

That system includes an H-bridge driver 230 with the emitter 80 of infrared source unit 28 connected across its outputs and timing circuits collectively identified by reference character 232. Circuits 232 supply timing signals to driver 230. The timing signals are derived from a, crystal oscillator (not shown) and then counted down to provide the desired pulse rate and duty cycle. A current implementation uses a 7 MHz oscillator to provide a 85.45 Hz pulse rate and 7.1 percent duty cycle.

The driver contains logic circuits and power MOSFETs arranged in the so-called "H" configuration. This provides the capability to turn on opposite legs of the "H" so that the infrared radiation emitter 80 is easily driven in opposite directions. The magnitude of the voltage applied to the source is controlled by changing the input voltages $+Vp$ and $-Vp$.

Figure 11:
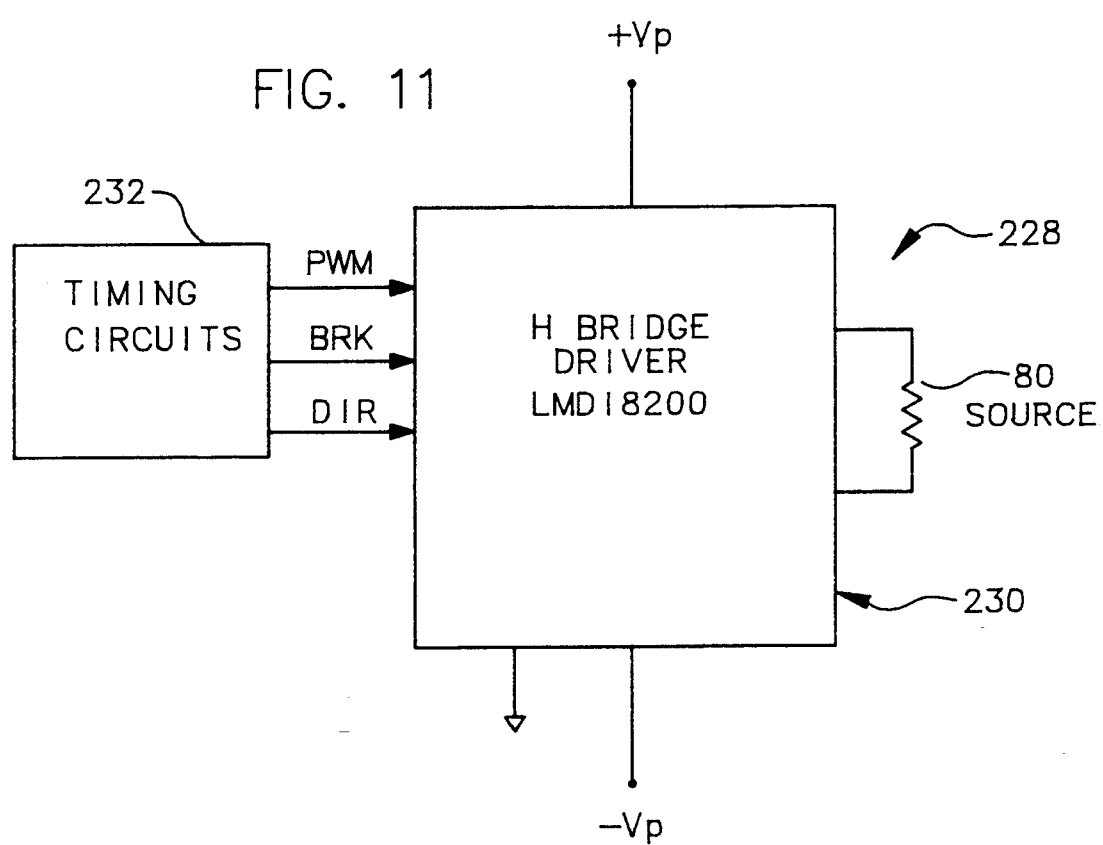
FIG. 11 is a block diagram of an electronic driver for the infrared radiation emitter unit.

Bipolar pulsing, whether provided by the circuitry shown in FIG. 11 or in some other manner, is preferred. Pulsing of this character eliminates the hysteresis, migration of emitter materials, and other adverse effects of continually pulsing the emitter with energy of the same polarity.

The details of the bipolar power supply 228 illustrated in FIG. 11 are not part of the present invention. Consequently, they will not be alluded to further herein.

Referring now to FIG. 2, it will be remembered that the detector side of transducer 24 includes a detector unit 30 and a power supply 32 for supplying biasing voltage to the detector unit.

Detector unit 30 includes a boxlike housing 234 mounted on a printed circuit board 236. A monolithic, heat conductive, isothermal detector support 238 is installed in housing 234. This component is preferably fabricated from aluminum because of the high heat conductivity which that element possesses.

Isothermal support 238 has a generally L-shaped configuration with two normally related, integral legs 240 and 242 separated by a transition section 244. The isothermal support is installed in detector unit housing 234 with locating and retaining lugs 246, 248, and 250 in housing 234 engaged in cooperating recesses 252, 254, and 256. These are located in the leg 240, transition section 244, and leg 242 of isothermal support 238.

Supported from and mounted in isothermal support 238 are: (a) data and reference detectors 258 and 260, (b) a beam splitter 262, and (c) the detector heaters 264 and 266 and thermistor-type current flow-limiting device 268 of a detector heater system 270. This system is employed to keep the two detectors at exactly the same, selected temperature, typically with a tolerance of not more than 0.01° C.

Detectors 258 and 260 are preferably made from lead selenide because of the sensitivity which that material possesses to electromagnetic energy having wavelengths which are apt to be of interest. Detectors of an appropriate character are disclosed in detail in parent application Ser. No. 07/528,059.

Detectors 258 and 260 are supported from heat conductive support 238 along with beam splitter 262. The beam splitter has a generally parallelepipedal configuration and is fabricated from a material such as silicon or sapphire which is essentially transparent to electromagnetic energy with wavelengths of interest. The exposed front surface 272 of the beam splitter is completely covered with a coating (not shown) capable of reflecting to data detector 258 that infrared radiation impinging on the beam splitter which has a wavelength shorter than a selected value. Preferred is a proprietary coating supplied by Optical Coating Laboratories, Inc., Santa Rosa, Calif.

In the illustrated exemplary embodiment of the invention, beam splitter 262 will reflect to data detector 258 as indicated by arrow 274 in FIG. 2 energy having a wavelength shorter than about 4 microns. The energy of longer wavelengths is, instead, transmitted through the beam splitter to reference detector 260 as is suggested by arrow 276 in the same figure.

Optical bandpass filters 278 and 280 are mounted in isothermal support 238 in front of data and reference detectors 258 and 260. Bandpass filters 278 and 280 are also obtained from Optical Coating Laboratories, Inc.

In the exemplary application of the present invention disclosed herein in which carbon dioxide is the gas being monitored, the data detector bandpass filter 278 is centered on a wavelength of 4.260 $\mu$m and has a bandwidth of 0.10 $\mu$m. This is two times narrower than the band passed by filter 278. The carbon dioxide absorption curve is fairly narrow and strong, and bandpass filter 278 centers the transmission band within that absorption curve. Therefore, if there is a change in carbon dioxide level in the gas(es) being analyzed, the maximum modulation for a given change in carbon dioxide level is obtained. If the electromagnetic energy otherwise reached the data detector through the bandpass filter whether or not carbon dioxide was present in the gases being analyzed, the modulation of the carbon dioxide related output of data detector 258 would decrease; and accuracy would suffer.

The reference detector optical bandpass filter 280 in detector unit 30 is centered on a wavelength of 3.681 $\mu$m and has a half power bandwidth of 0.190 $\mu$m. That filter transmits maximum energy near the band absorbed by data detector 258; but there are no interfering gases that would absorb energy in the transmitted bandwidth. Thus, nitrous oxide and water, the gases most apt to interfere, absorb on opposite sides of that bandwidth; and the selected region is almost certain to be one where there is no absorption. This absorption of maximum energy in an adjacent bandwidth is selected so that the output from reference detector 260 will be at least as large as the output from data detector 258. This contributes markedly to the accuracy of the gas concentration indicative signal subsequently obtained by ratioing the data and reference signals.

All of that energy over the entire span of the infrared radiation beam reaching detector unit 30 with a wavelength shorter than the selected cutoff is reflected to data detector 258. Similarly, over the entire span of the beam, that energy with a longer wavelength is transmitted through beam splitter 262 to reference detector 260. Because of this, the physical relationship of detectors 258 and 260, and the identical dimensioning and configuration of the energy intercepting surfaces of those detectors, both detectors "see" the same image of the beam of infrared radiation. This contributes markedly to the accuracy afforded by detector unit 30.

Furthermore, the two signals to the data and reference detectors 258 and 260 are identical in time inasmuch as the detector-to-beam splitter distances are equal and the time required for the reflected and transmitted components of the beam to travel from beam splitter 262 to each of the two detectors 258 and 260 is, therefore, the same. By making the two detectors 258 and 260 spatially coincident in time from the optical viewpoint, the adverse effects on accuracy attributable to foreign material collecting on any of the optical windows 52, 54, 68, and 70 and a subsequently described window of detector unit 30 are also eliminated by the subsequent ratioing of the data and reference detector output signals.

The infrared radiation reaches beam splitter 262 through an aperture 282 in the front wall 284 of detector unit housing 234. A typically sapphire window 286 spans aperture 282 and keeps foreign material from penetrating to the interior 288 of detector unit housing 234 before the detector unit 30 is installed in transducer housing 26 and if that housing is subsequently unsealed.

To exclude extraneous energy, and thereby ensure that only the electromagnetic energy from emitter unit 28 reaches beam splitter 262, light traps 290 and 292 are provided. The first of these is a triangularly sectioned, inwardly extending, projection of monolithic, isothermal support 238. The second, cooperating light trap 294 is aligned with, fixed in any convenient fashion to, and extends inwardly from that casing-associated ledge or lip 294 of support 238 which supports beam splitter 262.

The operation of transducer 24 as thus far described is believed to be apparent from the drawing and the foregoing, detailed description of the invention.

Briefly, however, electromagnetic energy in the infrared portion of the spectrum is generated by heating the source or emitter 80 of emitter unit 28, preferably by applying bipolar pulses of electrical energy across the emitter unit as discussed above. The energy thus emitted is collated and focused into a beam by the mirrored parabolic surface 206. The thus formed beam of energy exits the emitter unit 28 through the central bore 200 in base 88 and a complementary central bore 296 in cap 84 and is propagated along optical path 50 across the gas(es) flowing through airway adapter 22.

Energy in a species specific band is absorbed by the gas of interest flowing through the airway adapter (typically carbon dioxide) to an extent proportional to the concentration of that gas. Thereafter, the attenuated beam passes through the aperture 282 in the front wall 284 of the detector unit casing 234, is intercepted by beam splitter 262, and is either reflected toward data detector 258 or transmitted to reference detector 260. The optical bandpass filters 278 and 280 in front of those detectors limit the energy reaching them to specified (and different) bands. Each of the detectors 258 and 260 therefore outputs an electrical signal proportional in magnitude to the intensity of the energy striking that detector. These signals are amplified by data detector and reference detector amplifiers (not shown) in detector unit 30 and then typically ratioed to generate a third signal accurately reflecting the concentration of the gas being monitored. The signal processor used for this purpose is independent of airway adapter 22 and transducer 24 and not part of the present invention. It will accordingly not be disclosed herein.

As discussed above, the preferred lead selenide detectors 258 and 260 are extremely temperature sensitive; and it is therefore critical that these two detectors be maintained at the same temperature, preferably with the above-mentioned tolerance of not more than 0.01° C. Also, it was pointed out above that this desired degree of control is readily available from the detector heating system 270 made up of data detector heater 264, reference detector heater 266, and thermistor-type, temperature-limiting control 268.

Heaters 264 and 266 in the illustrated detector unit 30 are precision, 25 ohm resistors with a tolerance of ±0.5 percent. Thermistor 268 is conventional.

Referring now specifically to FIG. 2, resistance heaters 264 and 266 are installed in circularly sectioned recesses 298 and 300 extending from side-to-side in the legs 240 and 242 of monolithic, isothermal support 238, producing efficient, conductive heat transfer between the heaters and the support. Thermistor 268 is installed in a similar, transversely extending, complementary aperture 302 in isothermal support transition section 244.

The spatial relationship between heater 264 and data detector 258 and between heater 266 and reference detector 260 are identical, and the spatial relationship between thermistor 268 and each of the heaters 264 and 266 is also identical. Furthermore, the two heaters 264 and 266 are so located with respect to the associated detectors 258 and 260 that the thermal energy emitted from the heaters travels first across the detectors and then across the current flow-limiting thermistor 268 to heat dumps provided by gaps 304 and 306. These are respectively located between: (a) the leg 240 of isothermal support 238 and the top wall 308 of detector unit housing 234, and (b) the rear wall 310 of the housing and the leg 242 of the isothermal support. The heat flow paths are identified by arrows 312 and 314 in FIG. 2. As a consequence of the foregoing and the high thermal conductivity of isothermal support 238, the data and reference detectors 258 and 260 can readily be maintained at the same temperature.

Figure 19:
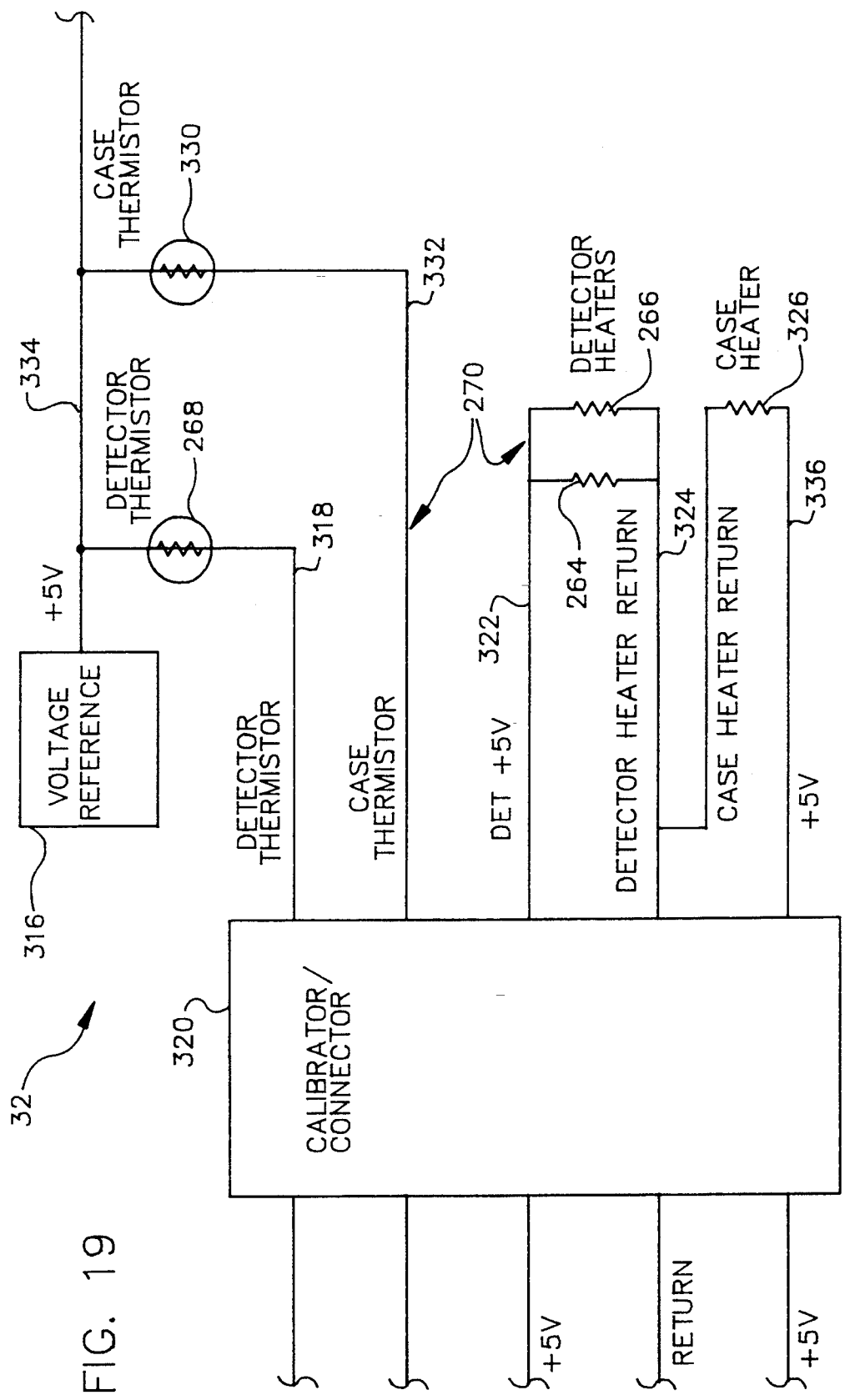
FIG. 19 is a block diagram of detector and case heater systems employed in the transducer shown in FIG. 1.

A wiring diagram for detector heating system 270 is shown in FIG. 19. Turning then to that figure, the data detector heater 264 and reference detector heater 266 are supplied with +5 V power from a voltage regulator 316 incorporated in power supply 32. This voltage is modulated by the thermistor 268 of heating system 270 to control the output from the detector heaters and maintain isothermal support 238—and therefore data and reference detectors 258 and 260—at a constant, uniform temperature.

Detector thermistor 268 is located in an external lead 318. That lead extends from voltage regulator 316 to a calibrator/connector 320 which may be located at some distance from transducer 24. Lead 322 and heater return 324 connect the external calibrator/connector 320 to the detector heaters 264 and 266.

Unit 320, the purposes for which it is provided, and the manner in which it functions are the subject of a separate application filed this date and identified by application Ser. No. 07/600,413. For that reason and because this unit is not part of the present invention or necessary to an understanding of the present invention, it will not be described in this specification.

It is another function of power supply 32 to supply electrical energy for biasing detectors 258 and 260. That is important because the sensitivity of those detectors to energy in the infrared portion of the electromagnetic spectrum is bias dependent. Therefore, as the bias is increased, the magnitude of the signal that can be outputted for a given quantum of impinging energy is increased. However, the signals outputted from the detectors are small; and signal-to-noise ratio is accordingly a significant consideration. Twenty volts is typically the maximum bias that can be applied to the detectors without increasing the signal-associated noise to an unacceptable level.

The circuitry employed in power supply 32 for detector biasing and the modus operandi of that circuitry are in detail disclosed in parent application Ser. No. 528,059.

It will be remembered that transducer 24 also includes a data detector signal amplifier and a reference detector signal amplifier for increasing the levels of the signals outputted by data detector 258 and reference detector 260.

Typically, transducers with detector units of the character disclosed herein are commonly used in environments in which electrical noise is prevalent. Electrostatic shielding is therefore preferably employed to isolate the data and reference detectors and associated circuitry from the adverse effects of EMI and other radiations in the ambient surroundings. This is yet another component of the transducer which is disclosed in parent application Ser. No. 528,509.

Parent application Ser. No. 528,509 also discloses a novel casing for housing the electrostatic shielding and the detectors and other electrical and optical components of the transducer and for keeping foreign matter from reaching those components. Guide systems in the casing and in the electrostatic shield facilitate the assembly of the unit and the electrical connection of the electrostatic shield to the components shielded by that device.

It was pointed out above that the just-described transducer 24 can be employed to advantage to measure the concentration of a designated gas flowing through the sampling passage 40 in airway adapter 22. As the monitoring of the gases proceeds, and with the airway adapter 22 at ambient temperature, moisture can condense out of the surrounding environment and collect on the optical windows 52 and 54 of the airway adapter and/or the windows 68, 70, and 286 of transducer 24. The result may be a degradation in performance and loss of accuracy.

This problem can be solved by maintaining the transducer housing 26 and the airway adapter 22 at an elevated temperature, preferably in the range of 42°–45° C. during the sampling process This is accomplished with a resistance-type heater 326. The casing heater is mounted in a recess 328 in the casing 26 of transducer 24. Resistance heater 326 keeps casing 26 and the airway adapter 22 assembled to transducer 24 at the desired temperature.

Operation of casing heater 326 is controlled by a thermistor 330 mounted on the heater and connected to calibrator/connector 320 by lead 332 (see FIG. 19).

Plus 5 V power is supplied to case heater 326 from the voltage regulator 316 in power supply 32 by way of external calibrator/connector 330 and lead 334. The opposite side of heater 326 is connected by casing heater return 336 to the return 324 from data and reference detector heaters 264 and 266.

Referring again to the drawing, FIGS. 12–18 depict a second infrared radiation source or emitter unit 338 also constructed in accord with, and embodying, the principles of the present invention.

The major components of emitter unit 338 are: (1) a base 340, (2) a lead frame 342, (3) an infrared radiation emitter or source 344, (4) conductive leads 346 and 348 for connecting emitter 344 across an appropriate power source, and (5) a mirror assembly 350 for collimating and projecting from unit 338 in the form of a beam infrared radiation outputted by emitter 344.

Emitter 344 may be a duplicate of the emitter 80 discussed above.

The base 340 of emitter unit 338 is a generally cylindrical component with a central aperture 352 through which the beam of infrared radiation formed and projected by mirror assembly 350 can escape to the exterior of unit 338. Like its complement in emitter unit 28, base 340 is preferably fabricated from a polysulfone or other polymer resistant to high temperatures.

Figure 16:
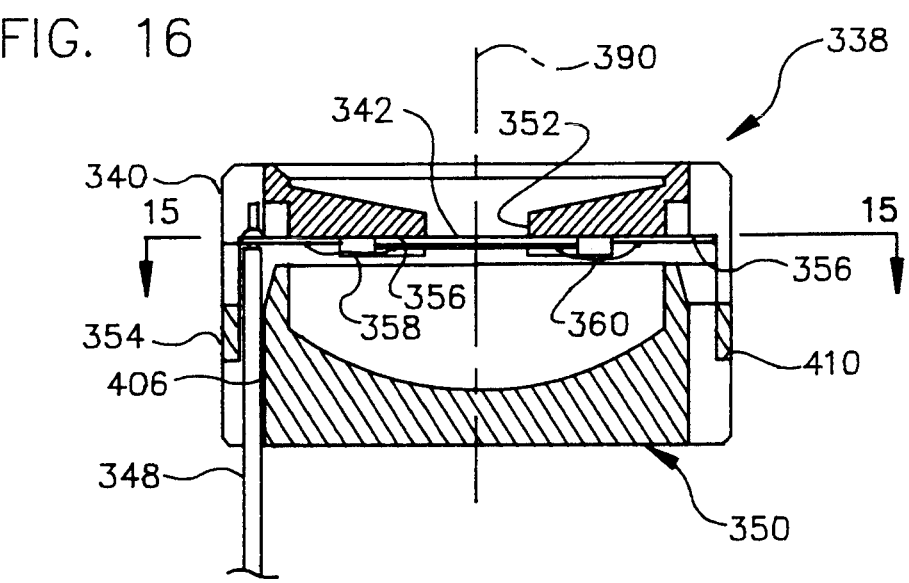
FIG. 16 is a section through the source, taken substantially along line 16—16 of FIG. 12.

With emitter unit 338 in the orientation shown in FIGS. 12, 13, and 16, base 340 has a vertically oriented, circular side wall 354; an internal, horizontal ledge 356 surrounded by a side wall 354, and diametrically opposed locator lugs 358 and 360.

Figure 17:
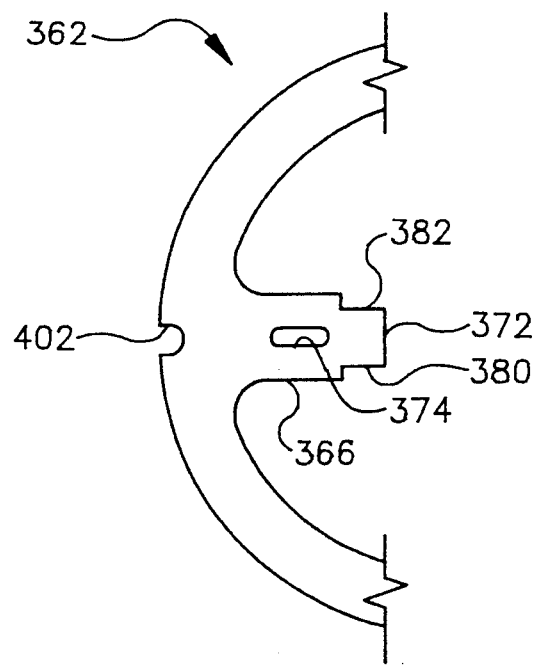
FIG. 17 is a fragmentary plan view of a lead frame component employed in the device of FIG. 12.
Figure 18:
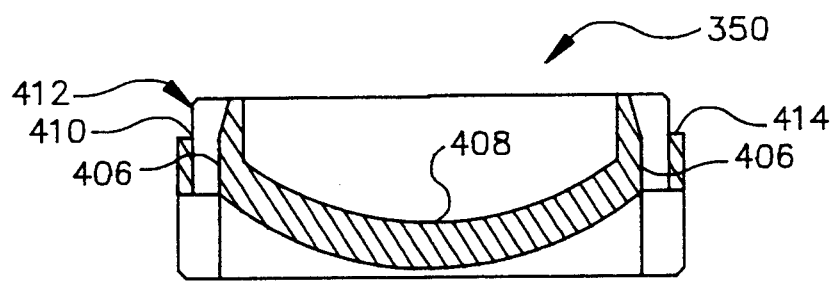
FIG. 18 is a vertical section through a parabolic mirror component employed in the infrared radiation source to collimate, focus into a beam, and direct along a specific optical path infrared radiation outputted by the emitter unit.

As is best shown in FIGS. 16 and 17, the lead frame 342 employed in unit 338 is made up of two identical, arcuate segments 362 and 364. Like their counterparts in unit 28, they may be fabricated from tin plated copper. From the practical viewpoint, this employment of identical lead frame segments is important in that it reduces the number of parts that must be stocked. Lead frame segments 362 and 364 are also simpler and therefore considerably cheaper to fabricate than the more complicated, integrated lead frame 82 employed in emitter unit 28.

Each of the lead frame segments 362 and 364 has an integral, inwardly extending, emitter support 366 with an emitter receiving groove 368. The groove opens onto the bottom sides 370 of the lead frame segments 362 and 364 and extends to the free ends 372 of emitter supports 366.

Formed in each of the emitter supports 366 adjacent its emitter receiving recess or groove 368 is an elongated, radially extending slot 374. With the commutator segments 362 and 364 installed in base 340 and seated on the ledge 356 of that base as shown in FIG. 15, the locator lugs 358 and 360 of base 340 extend through the slots 374 in emitter supports 366. That locates lead frame segments 362 and 364 relative to base 340.

Figure 14:
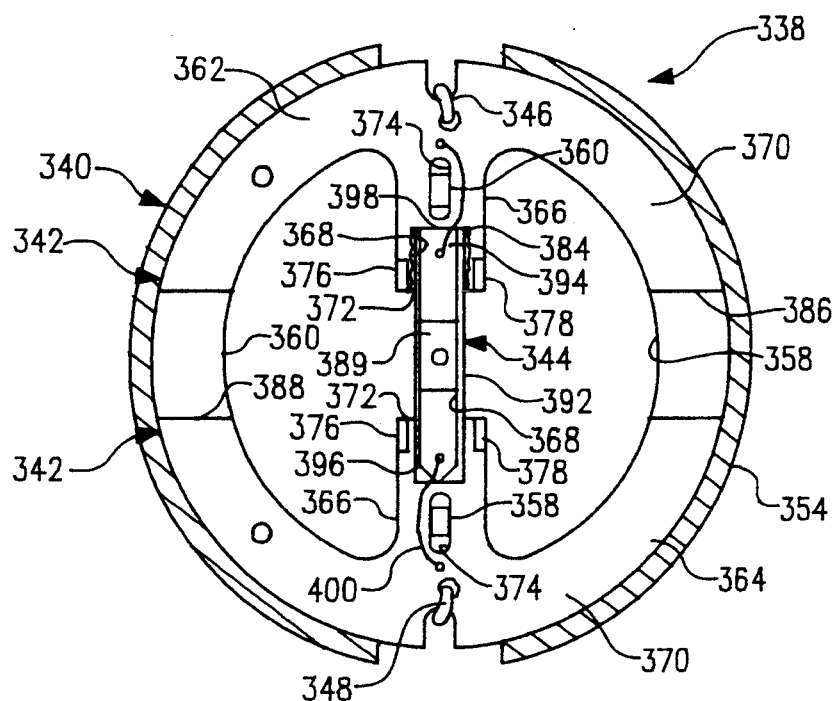
FIG. 14 is a section through the infrared radiation source shown in FIG. 12 taken substantially along lines 14—14 of FIG. 13.

Also employed to locate lead frame segments 362 and 364 in the base 340 of emitter unit 338 are cooperating pairs of depending, integral lugs 376 and 378. These are found at the ends of each lead frame segment's emitter support 366. With the lead frame segments assembled to emitter base 340 as shown in FIGS. 14–16, lugs 376 and 378 fit into complementary notches 380 and 382. These notches are located on opposite sides, and at the free ends 372, of the emitter supports. The sides of the notches thereby embrace the opposite sides of the supports 366 to hold in place the lead frame segments 362 and 364 in which those supports are incorporated.

Once installed, lead frame segments 362 and 364 are bonded in place and to emitter base 340 by an appropriate adhesive applied at the locations indicated by reference character 384 in FIG. 16. With the two lead frame segments 362 and 364 installed in emitter 344 in the manner just described, they are electrically isolated by the gaps 386 and 388 between the segments.

After lead frame segments 362 and 364 have been installed in base 340, emitter 344 is added to the assembly. It is seated in those emitter-receiving grooves 368 located in the lead frame segment-provided emitter supports 366 with the emissive layer 389 of the emitter centered on the longitudinal centerline 390 of unit 338 and spanning the gap 392 between the ends of emitter supports 366.

End 394 of emitter 344 is bonded to its support 366. But, as in emitter unit 28, the opposite end 396 of the emitter is not. This leaves emitter 344 free to grow or expand longitudinally as it heats up during operation; and this keeps from there being imposed on the emitter stresses which might damage or destroy it.

Emitter 344 is electrically connected to lead frame segments 362 and 364 after it is installed by electrical leads 398 and 400. At one end, lead 398 is soldered to lead frame segment 362. The other end of the lead is soldered to the terminal 94 at the fixed end 394 of the emitter. Lead 400 is similarly soldered at opposite ends to lead frame segment 364 and the terminal 96 at the opposite, floating end 396 of emitter 344.

External leads 346 and 348 extend upwardly along the inside of base side wall 354 and into diametrically opposed, semicircular recess 402 and 404 in the rims of lead frame segments 362 and 364. Here, they are soldered to the commutator segments.

With the electrical connections just described completed, current supplied from the external source flows from external lead 346 through lead frame segment 362, lead 398, emitter terminal 94, the electrically resistive, emissive layer 389 of the emitter, emitter terminal 96, lead 400, and lead frame segment 364 to external lead 348 or through the same set of components but in the opposite direction. In both cases, the current flowing through emissive layer 389 causes the latter to heat up and output the wanted infrared radiation.

The final, and typically last to be installed, major component of emitter unit 338 is mirror component 350.

This component, shown in FIGS. 12, 13, 16, and 18, has a circular cross-section of the same diameter as base 340. It is typically fabricated from ABS polymer or a polymer with comparable characteristics.

Grooves extending from end-to-end of mirror component 350 accommodate the external leads 346 and 348 of emitter unit 338. One of these grooves is shown in FIG. 16 and identified by reference character 406.

The upper surface 408 of mirror component 350 has a parabolic configuration. Surface 408 is plated first with copper and then with gold to provide a mirror for collating the energy from emitter 344 and then focusing that infrared radiation into a beam projected from the emitter unit.

A groove 410 extends around the periphery of mirror component 350. With the mirror component assembled to the base 340 of emitter unit 338, the side wall 354 of the base surrounds the upper part 412 of mirror component 350. This protects mirrored surface 408 from damage.

The lower end 414 of groove 410 also provides a seat for base 340. This keeps emitter 344 from engaging and perhaps being damaged by base 340.

The invention may be embodied in many other specific forms in addition to those disclosed above without departing from the spirit or essential characteristics of the invention. The disclosed embodiments are therefore to be considered in all respects as illustrative and not restrictive. The scope of the invention is instead indicated by the appended claims, and all changes which come within the meaning and range of equivalency of the claims are therefore intended to be embraced therein.

We claim:

1. A system for generating periodic pulses of infrared radiation, said system comprising:

an emitter means which is resistive to the flow of electrical current therethrough and can accordingly be heated to an elevated temperature and caused to emit infrared radiation by applying an electrical voltage thereacross; and means for applying electrical pulses of first one, and then the opposite, polarity to said emitter means to heat said emitter means as aforesaid to effect the emission of said pulses of infrared radiation therefrom.

2. An infrared radiation source which includes an emitter means and a support for said emitter means, said emitter means including a substrate and an emissive, electrically resistive material on said substrate and said source also including means for fixing one end only of said substrate to said support, whereby said emitter means is free to expand and contract without resistance as said emissive material is respectively heated to an operating temperature and cools to a lower temperature.

3. An infrared radiation source as defined in claim 2:
which includes a base mounting said emitter means support and a mirror means for collimating infrared radiation emitted from said emitter means into a beam;
said mirror means having an axis of symmetry and the means for fixing said one end of the emitter means to said support having the capability of automatically aligning the midpoint of the emitter means emissive layer with the axis of symmetry of the mirror means as the emitter means is fixed to the support.

4. An infrared radiation source as defined in claim 3 in which:
the emitter means support has first and second, spaced apart, diametrically opposed means for respectively supporting the fixed and opposite, floating end of the emitter means;
the means for fixing said one end of the emitter means to the first of the supporting means comprises a layer of adhesive on that supporting means; and
there is an aperture through said support at the location occupied by the fixed end of said emitter means when the emissive layer of the emitter means is centered as aforesaid;
whereby, when said emitter means is assembled to said support, said adhesive will flow toward said aperture and draw the emitter means toward said aperture by surface tension but will stop at said aperture, thereby halting said emitter means with its emissive layer centered as aforesaid.

5. An infrared radiation source which comprises:
emitter means having a substrate; a layer of an electrically resistive, emissive material on said substrate; and first and second electrical terminals on said substrate and in electrical contact with said layer of emissive material at the opposite ends thereof;
a base;
a lead frame with two electrically isolated segments supported along with said emitter means from said base; and
means providing electrical connections between the first emitter means terminal and one of said lead frame segments and between the second of said terminals and the other of the lead frame segments.

6. An infrared radiation source as defined in claim 5 in which the lead frame has two independent, arcuate segments, the length of said segments being such that, when the lead frame is assembled to the base, there are gaps between the ends of said segments.

7. An infrared radiation source as defined in claim 5:
which has a mirror means for collimating infrared radiation outputted by said emitter means and focusing said radiation into a beam;
said mirror means being supported by said base and having an axis of symmetry; and
the midpoint of the emitter material means emissive layer being coincident with the axis of symmetry of the mirror means.

8. An infrared radiation source as defined in claim 7 which has means for so spacing said emitter means from said mirror means as to keep the emitter means from contacting and damaging the mirror means.

9. An infrared radiation source as defined in claim 5 in which the lead frame has terminals integral with the respective segments of the lead frame and said base has terminal receiving slots for said terminals, said slots extending from end to end of the base.

10. An infrared radiation source as defined in claim 5 which has a protective cap assembled to said base in overlying relationship to said emitter means.

11. An infrared radiation source as defined in claim 10 which:
has a mirror means for collimating infrared radiation outputted by the emitter means and for focusing the collimated radiation into a beam; and
wherein there are aligned apertures in said base and said cap through which said beam of infrared radiation can pass to the exterior of the source.

12. A transducer which comprises:
an infrared radiation source as defined in claim 5 for outputting a beam of infrared radiation;
detector means for intercepting said beam after it has passed through a sample and been attenuated by a selected gas of interest in said sample; and
means for housing said infrared radiation source and said detector means in an aligned relationship along a selected optical path.

13. The combination of an airway adapter and a transducer for outputting an electrical signal which is indicative of the concentration of a selected gas in a stream flowing through the airway adapter;
said airway adapter having a sampling passage therethrough and optical windows on opposite sides of said sampling passage and aligned along an optical path traversing the sampling passage;
said transducer having: an infrared radiation source as defined in claim 5 for generating infrared radiation and propagating a beam of said radiation along said optical path and detector means for intercepting said beam after it has traversed said sampling passage and for outputting a signal which is indicative of the extent to which the infrared radiation is attenuated as it traverses the sampling passage and, consequentially, of the concentration of the selected gas in the stream flowing through the sampling passage; and
said airway adapter and said transducer having cooperating means for detachably fixing said transducer to said airway adapter with said infrared radiation source and said detector means on opposite sides of the airway adapter and aligned along the optical path.

14. A system for analyzing the concentration of a selected gas in a sample which may contain that gas, said system including an infrared radiation source as defined in claim 5 for emitting infrared radiation and means for forming and directing a beam of said radiation through said sample to thereby attenuate said infrared radiation to an extent proportional to the concentration of the selected gas in said sample; and
detector means for intercepting the attenuated beam of infrared radiation and outputting a signal proportional in magnitude to the concentration of the selected gas in the sample.

15. A system as defined in claim 14 in which the detector means comprises:

first and second detectors upon which said beam of attenuated infrared radiation can impinge;

a first filter means in front of said first detector for limiting the infrared radiation reaching the first detector to infrared radiation in that part of the electromagnetic spectrum containing energy absorbable by the selected gas;

a second filter means in front of said second detector for limiting the infrared radiation reaching that detector to infrared radiation in a selected part of the electromagnetic spectrum containing energy which is not absorbable by the selected gas; and a beam splitter for transmitting said attenuated beam of infrared radiation to one of said first and second detectors and for reflecting said beam onto the other of said first and second detectors.

16. A system as defining in claim 15 which has a driver means for applying electrical pulses of first one polarity and then the opposite polarity to said emissive layer to effect the emission of pulses of infrared radiation therefrom.

17. That method of manufacturing an infrared radiation source which includes the steps of:

providing an infrared radiation emitter which includes a substrate and a layer of an emissive, electrically resistive material on said substrate;

providing a centrally apertured, electrically conductive lead frame;

fixing said infrared radiation emitter to said lead frame with the emitter spanning the central aperture in the lead frame;

electrically connecting opposite ends of the emissive material layer of the infrared radiation source to said lead frame on opposite sides of the aperture therein;

installing the assembly of infrared radiation emitter and lead frame in a base; and then interrupting the continuity of said lead frame at locations on opposite sides of the lead frame and between the infrared radiation emitter-to-lead frame connections to thereby divide the lead frame into two electrically isolated segments and create a circuit in which an electrical current applied to one of said segments flows therefrom through the layer of emissive, electrically resistive material to the other of the lead frame segments.

18. A method as defined in claim 17 in which:

the lead frame is a flat member having integral terminals extending from the segments of the lead frame;

the base has terminal receiving slots opening onto the periphery thereof; and said terminals are bent to fit into said slots.

19. A method as defined in claim 18 in which:

the lead frame is an integral ring-shaped member with breakaway tabs separating the lead frame segments; and the lead frame is divided into electrically isolated segments as aforesaid by removing said breakaway tabs.

20. A method as defined in claim 17:

in which there are terminals at the opposite ends of and electrically connected to the emissive material layer of the infrared radiation emitter; and the electrical connections between the emissive layer and the lead frame are made between said terminals and the segments of the lead frame and after the lead frame and emitter are installed in the base.

21. A method as defined in claim 17 which includes the step of thereafter assembling a protective cap to said base on the exposed side of the infrared radiation emitter.

22. A method as defined in claim 17 which includes the step of assembling to said base and in axial alignment with the emitter a component with a mirror means for collimating infrared radiation outputted from the emitter and for focusing said radiation into a beam.

23. A method as defined in claim 17 which includes the steps of providing on said base and in said lead frame complementary sets of locator lugs and slots so asymmetrically arrayed that the assembly of lead frame and infrared radiation emitter can not be assembled to said base in an upside down orientation.

24. That method of manufacturing an infrared radiation source which includes the steps of:

providing a base and an infrared radiation emitter which includes a substrate and a layer of an emissive, electrically resistive material on said substrate;

providing a lead frame which has two independent, arcuate segments;

installing said segments in said base at one end thereof with the segments concentrically arranged about the axial centerline of the base and with gaps between the ends of the segments;

installing the infrared radiation emitter in the base on the lead frame; and making electrical connections between the ends of the emissive material layer of the infrared radiation emitter and the lead frame segments, thereby creating a circuit in which an electrical current applied to one of said segments flows therefrom through the layer of emissive, electrically resistive material to the other of the lead frame segments.

25. A method as defined in claim 24:

in which said base has recesses for electrical leads extending from the locus of the lead frame to the opposite end of the base; and after said lead frame is installed in the base, installing leads in said recesses and electrically connecting the leads to the lead frame segments.

26. A method as defined in claim 25 which includes the step of thereafter assembling to said base and in axial alignment with the emitter a component with a mirror means for collimating infrared radiation outputted from the emitter and for focusing said radiation into a beam.

27. A method as defined in claim 24:

in which there are terminals at the opposite ends of and electrically connected to the emissive material layer of the infrared radiation emitter; and the electrical connections between the emissive material layer and the lead frame are made between said terminals and the segments of the lead frame and after the lead frame and emitter are installed in the base.

28. A method as defined in claim 24 which includes the step of assembling a protective cap to said base on the exposed side of the infrared radiation emitter.

29. A device which can be converted into an infrared radiation source, said device comprising:

emitter means having a substrate; a layer of an electrically resistive, emissive material on said substrate; and first and second electrical terminals on said substrate and in electrical contact with said layer of emissive material at the opposite ends thereof;

a base;

a lead frame with two electrically isolatable segments supported along with said emitter means from said base; and means providing electrical connections between the first emitter means terminal and one of said lead frame segments and between the second of said terminals and the other of the lead frame segments.

30. A device as defined in claim 29 wherein said lead frame is an integral annular ring with removable tab means which can be removed after said leaf frame is assembled to said base to divide said lead frame into two separate segments with gaps between the ends thereof.

31. A device as defined in claim 30:

which comprises means for assembling said emitter means to said lead frame with one end of the emitter means fixed relative to the lead frame and the other end thereof free to float relative to said lead frame, said lead frame thereby serving as both a support and an assembly jig for the emitter means; and said lead frame and said base having cooperating means which so engage as the emitter means support is assembled to the base as to keep said emitter means from being assembled to said base other than in a single selected orientation relative to the base.

32. A device as defined in claim 31 in which:

said base has a platform for supporting the lead frame, a circular wall surrounding said platform, and an asymmetric array of locator lugs protruding radially from said wall; and said lead frame is a flat member with a circular configuration, has a diameter such that it can be seated on said platform and positioned thereon by said wall, and has in the rim thereof a set of slots complementing and positioned to receive the locator lugs of the base.

33. An infrared source which comprises:

an emitter unit comprising an electrically driven emitter means, a support for said emitter means, and a base;

said emitter means support comprising a lead frame with a rim or terminals for connecting said emitter means across an electrical power source; and said base and said lead frame having cooperating means which keep said emitter unit from being assembled to said base in other than a single orientation relative to said base.

34. An infrared radiation source as defined in claim 33 in which:

said base has a lead frame supporting platform, a circular wall surrounding said platform, and an asymmetric array of locator lugs protruding radially from said wall; and said lead frame is a flat member with a circular configuration, has a diameter such that it can be seated on said platform and positioned thereon by said wall, and has in the rim thereof a set of slots complementing and positioned to receive the locator lugs of the base.

35. An infrared radiation source as defined in claim 33:

which has a mirror means for collimating and focusing electromagnetic energy outputted by said emitter means; and in which:

said base has a central bore therethrough;

said mirror means is disposed in said central bore; and said mirror means and said base have cooperating means which locate said mirror means in said bore in optically aligned relationship with the emitter means of the emitter unit.

36. An infrared radiation source as defined in claim 35 in which the cooperating means of the base and the mirror means is an array of complementary lugs and recesses.

37. An infrared radiation source as defined in claim 35 which includes means spacing said mirror means form said emitter means and thereby keeping the emitter means and the mirror means from coming into damage-producing contact.

38. An infrared radiation source as defined in claim 33:

which includes a cap assembled to said base in overlying protective relationship to said base, said cap having: an aperture through which infrared radiation emanating from said emitter means can be propagated and means receiving the lead frame terminals; and said cap and said base having cooperating slots and wall segments which fix the cap relative to the base.

* * * * *